(12) United States Patent
Schaefer et al.

(10) Patent No.: US 9,079,872 B2
(45) Date of Patent: Jul. 14, 2015

(54) PHENANTHRO[9, 10-B]FURANS FOR ELECTRONIC APPLICATIONS

(75) Inventors: Thomas Schaefer, Liestal (CH);
Christian Schildknecht, San Diego, CA (US); Peter Murer, Oberwil (CH);
Christian Lennartz, Schifferstadt (DE);
Nicolle Langer, Heppenheim (DE);
Gerhard Wagenblast, Wachenheim (DE); Stefan Metz, Mannheim (DE)

(73) Assignee: BASF SE, Ludwigshafen (DE)

( * ) Notice: Subject to any disclaimer, the term of this patent is extended or adjusted under 35 U.S.C. 154(b) by 236 days.

(21) Appl. No.: 13/252,482

(22) Filed: Oct. 4, 2011

(65) Prior Publication Data
US 2012/0095222 A1    Apr. 19, 2012

Related U.S. Application Data

(60) Provisional application No. 61/390,622, filed on Oct. 7, 2010.

(51) Int. Cl.
*C07D 307/77* (2006.01)
*C07D 405/14* (2006.01)

(52) U.S. Cl.
CPC ............ *C07D 307/77* (2013.01); *C07D 405/14* (2013.01)

(58) Field of Classification Search
CPC ............................ C07D 307/77; C07D 405/14
See application file for complete search history.

(56) References Cited

U.S. PATENT DOCUMENTS

| | | | |
|---|---|---|---|
| 5,077,142 A | 12/1991 | Sakon et al. | |
| 6,097,147 A | 8/2000 | Baldo et al. | |
| 6,413,656 B1 | 7/2002 | Thompson et al. | |
| 6,420,057 B1 | 7/2002 | Ueda et al. | |
| 6,451,415 B1 | 9/2002 | Forrest et al. | |
| 6,451,455 B1 | 9/2002 | Thompson et al. | |
| 6,458,475 B1 | 10/2002 | Adachi et al. | |
| 6,515,298 B2 | 2/2003 | Forrest et al. | |
| 6,573,651 B2 | 6/2003 | Adachi et al. | |
| 6,828,044 B2 | 12/2004 | Conley | |
| 7,183,010 B2 | 2/2007 | Jarikov | |
| 2001/0015432 A1 | 8/2001 | Igarashi | |
| 2001/0019782 A1 | 9/2001 | Igarashi et al. | |
| 2002/0024293 A1 | 2/2002 | Igarashi et al. | |
| 2002/0048689 A1 | 4/2002 | Igarashi et al. | |
| 2002/0055014 A1 | 5/2002 | Okada et al. | |
| 2002/0094453 A1 | 7/2002 | Takiguchi et al. | |
| 2002/0100906 A1 | 8/2002 | Takiguchi et al. | |
| 2002/0121638 A1 | 9/2002 | Grushin et al. | |
| 2002/0197511 A1 | 12/2002 | D'Andrade et al. | |
| 2003/0017361 A1 | 1/2003 | Thompson et al. | |
| 2003/0040627 A1 | 2/2003 | Fujii | |
| 2003/0054198 A1 | 3/2003 | Tsuboyama et al. | |
| 2003/0059646 A1 | 3/2003 | Kamatani et al. | |
| 2003/0068526 A1 | 4/2003 | Kamatani et al. | |
| 2003/0068528 A1 | 4/2003 | Thompson et al. | |
| 2003/0068535 A1 | 4/2003 | Takiguchi et al. | |
| 2003/0072964 A1 | 4/2003 | Kwong et al. | |
| 2003/0124381 A1 | 7/2003 | Thompson et al. | |
| 2003/0141809 A1 | 7/2003 | Furugori et al. | |
| 2009/0066226 A1 | 3/2009 | Sugita et al. | |
| 2009/0105447 A1 | 4/2009 | Schafer et al. | |
| 2009/0309068 A1 | 12/2009 | Schafer et al. | |
| 2010/0039024 A1 | 2/2010 | Wendeborn et al. | |
| 2010/0109514 A1 | 5/2010 | Schäfer et al. | |
| 2010/0213834 A1 | 8/2010 | Molt et al. | |
| 2010/0249349 A1 | 9/2010 | Chebotareva et al. | |
| 2011/0089407 A1 | 4/2011 | Schmidhalter et al. | |

FOREIGN PATENT DOCUMENTS

| | | |
|---|---|---|
| EP | 1 067 165 A2 | 1/2001 |
| EP | 1 191 612 A2 | 3/2002 |
| EP | 1 191 613 A2 | 3/2002 |
| EP | 1 211 257 A2 | 6/2002 |
| EP | 1 238 981 A2 | 9/2002 |
| EP | 1 239 526 A2 | 9/2002 |
| EP | 1 244 155 A2 | 9/2002 |
| EP | 1 970 976 A1 | 9/2008 |
| EP | 1 998 388 A1 | 12/2008 |
| EP | 2 034 538 A1 | 3/2009 |
| EP | 1 885 818 B1 | 1/2010 |
| JP | 2003-59667 | 2/2003 |
| JP | 2003-73387 | 3/2003 |
| JP | 2003-73388 | 3/2003 |
| JP | 2003-73665 | 3/2003 |

(Continued)

OTHER PUBLICATIONS

International Search Report issued Nov. 7, 2011 in PCT/EP2011/067255.
William M. Horspool, et al., "Substituent and Wavelength Effects in the Photochemistry of 5,6,7,8-Tetrachloro-3a,9a-Dihydro-2,3,9a-triarylfuro(2,3-b)(1,4)Benzodioxin Derivatives", Tetrahedron Letters, XP55010655, vol. 24, No. 35, Jan. 1, 1983, pp. 3745-3748.
U.S. Appl. No. 13/378,878, filed Dec. 16, 2011, Schildknecht, et al.
U.S. Appl. No. 14/115,934, filed Nov. 6, 2013, Wagenblast, et al.
U.S. Appl. No. 14/123,530, filed Dec. 3, 2013, Koenemann, et al.
U.S. Appl. No. 14/385,696, filed Sep. 16, 2014, Welker, et al.

*Primary Examiner* — Brian McDowell
(74) *Attorney, Agent, or Firm* — Oblon, McClelland, Maier & Neustadt, L.L.P.

(57) ABSTRACT

The present invention relates to an electronic device, especially an electroluminescent devices, comprising a compound of the formula

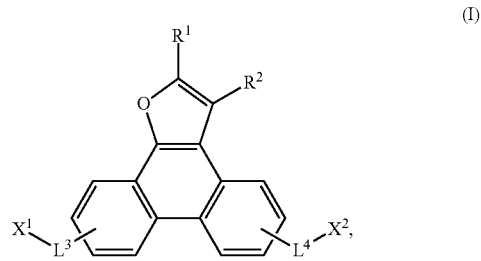

(I)

especially as host for phosphorescent compounds. The hosts may function with phosphorescent materials to provide improved efficiency, stability, manufacturability, or spectral characteristics of electroluminescent devices.

7 Claims, No Drawings

(56) References Cited

FOREIGN PATENT DOCUMENTS

| | | |
|---|---|---|
| WO | WO 99/47474 | 9/1999 |
| WO | WO 00/57676 | 9/2000 |
| WO | WO 00/70655 | 11/2000 |
| WO | WO 01/39234 A2 | 5/2001 |
| WO | WO 01/41512 A1 | 6/2001 |
| WO | WO 01/93642 A1 | 12/2001 |
| WO | WO 02/02714 A2 | 1/2002 |
| WO | WO 02/15645 A1 | 2/2002 |
| WO | WO 02/060910 A1 | 8/2002 |
| WO | WO 02/071813 A1 | 9/2002 |
| WO | WO 02/074015 A2 | 9/2002 |
| WO | WO 2005/019373 A2 | 3/2005 |
| WO | WO 2005/113704 A2 | 12/2005 |
| WO | WO 2006/000544 A2 | 1/2006 |
| WO | WO 2006/056418 A2 | 6/2006 |
| WO | WO 2006/067074 A1 | 6/2006 |
| WO | WO 2006/097419 A1 | 9/2006 |
| WO | WO 2006/100298 A1 | 9/2006 |
| WO | WO 2006/115301 A1 | 11/2006 |
| WO | WO 2006/121811 A1 | 11/2006 |
| WO | WO 2007/074093 A1 | 7/2007 |
| WO | WO 2007/090773 A1 | 8/2007 |
| WO | WO 2007/095118 A2 | 8/2007 |
| WO | WO 2007/101820 A1 | 9/2007 |
| WO | WO 2007/115970 A1 | 10/2007 |
| WO | WO 2007/115981 A1 | 10/2007 |
| WO | WO 2008/000727 A1 | 1/2008 |
| WO | WO 2008/031743 A1 | 3/2008 |
| WO | WO 2008/034758 A2 | 3/2008 |
| WO | WO 2008/101842 A1 | 8/2008 |
| WO | WO 2008/119666 A1 | 10/2008 |
| WO | WO 2009/003898 A1 | 1/2009 |
| WO | WO 2009/003919 A1 | 1/2009 |
| WO | WO 2009/100991 A1 | 8/2009 |
| WO | WO 2010/056669 A1 | 5/2010 |
| WO | WO 2010/079051 A1 | 7/2010 |
| WO | WO 2010/086089 A1 | 8/2010 |
| WO | WO 2010/129323 A1 | 11/2010 |
| WO | WO 2010/145991 A1 | 12/2010 |
| WO | WO 2011/073149 A1 | 6/2011 |

PHENANTHRO[9, 10-B]FURANS FOR ELECTRONIC APPLICATIONS

CROSS REFERENCE TO RELATED APPLICATIONS

The present application claims priority to U.S. Provisional Application 61/390,622, filed Oct. 7, 2010.

DESCRIPTION

The present invention relates to an electronic device, especially an electroluminescent device, comprising a compound of the formula I, especially as host for phosphorescent compounds. The hosts may function with phosphorescent materials to provide improved efficiency, stability, manufacturability, or spectral characteristics of electroluminescent devices.

U.S. Pat. No. 5,077,142 relates to electroluminescent devices comprising an anode and a cathode sandwiching ≥1 organic layer(s) in which the organic layer(s) include a compound represented by the general formula $(B)_m\text{-}(A)_n$ (B= selected cyclic hydrocarbons, condensed polycyclic hydrocarbons, O-contg. heterocycles, N-contg. heterocycles, and S-contg. heterocycles; A= benzene, biphenyl, methoxybenzene, or naphthalene groups; m= an integer in the range 1-6; and n= an integer in the range 1-6). The following compound is explicitly disclosed:

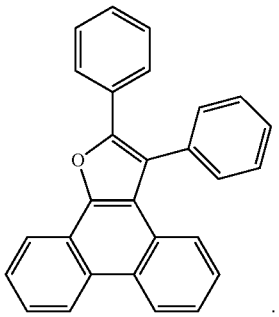 [SMILES: c1ccc(-c2oc3c4ccccc4c4ccccc4c3c2-c2ccccc2)cc1]

EP1067165 describes organic electroluminescent elements comprising a light emitting layer comprised of ≥1 thin layers of an organic compound put between an anode and a cathode in which ≥1 org. compound thin layer contains an organometallic complex having both an ionic coordinate bond formed by a nitrogen anion (e.g., included in an arom. heterocyclic ring) and a metal cation and a coordinate bond formed between a nitrogen atom or a chalcogen and a metal. The metal cation of the organic metal complex may be selected from Al, Ga, In, Tl, Be, Mg, Sr, Ba, Ca, Zn, Cd, Hg, Pd, or Cu. The following metal complexes are explicitly disclosed:

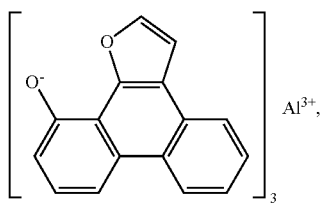
XXIV-3

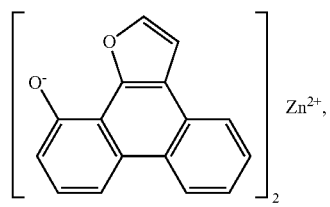
XXIV-6

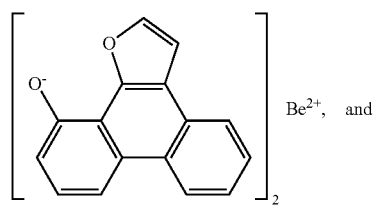
XXIV-11

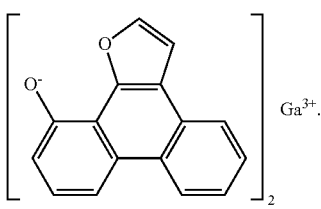
XXIV-12

U.S. Pat. No. 7,183,010 relates to org. light-emitting devices which comprise a substrate; an anode and a cathode disposed over the substrate; a luminescent layer disposed between the anode and the cathode are described in which the luminescent layer includes a host and 1 dopant; the host including a solid org. material comprising a mixt. of 2 components including a first component that is an org. compd. capable of transporting either electrons and/or holes and of forming both monomer state and an aggregate state and a second component of that is an org. compd. that upon mixing with the first host component is capable of forming a continuous and substantially pin-hole-free layer, while the dopant of is selected to produce light from the light-emitting device. Dinaphtho[1',2':2,3;2",1":10,11]perylo[1,12]furan (194-45-6; Tetrabenzo[1,2:5,6:7,8:11,12]pentapheno[13,14-bcd]furan (8Cl,9Cl)) is explicitly disclosed

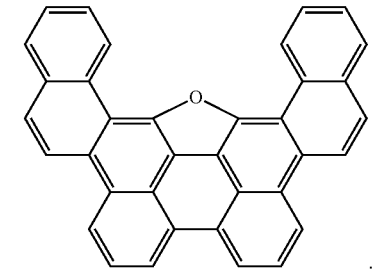 [SMILES: c1ccc2c(c1)ccc1c3cccc4c5cccc6c7ccc8ccccc8c7c7oc(c21)c(c34)c7c65]

U.S. Pat. No. 6,828,044 describes a device wherein the dopant comprises a benzofurane as represented by the following formula

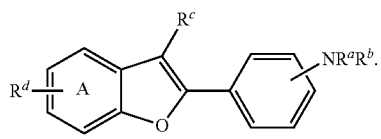

$R^a$ and $R^b$ independently represent an aryl or heteroaryl group and the nitrogen to which they are bonded is located at the 3- or 4-position of the phenyl ring; and $R^c$ represents hydrogen or an alkyl, aryl or heteroaryl group; and $R^d$ represents one or more hydrogen or alkyl, substituted nitrogen, aryl or heteroaryl groups which may join to form a ring fused to ring A.

WO2006097419 describes polymers which can contain repeating units of formula

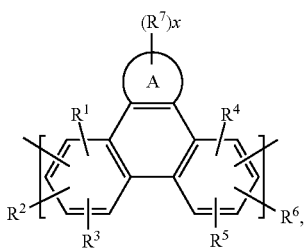

wherein A is a 5-, 6-, or 7-membered heteroaromatic ring, containing at least one heteroatom selected from nitrogen, oxygen and sulfur, especially one nitrogen atom and at least one further heteroatom selected from nitrogen, substituted nitrogen, oxygen and sulfur.

WO2007/090773 relates to polymers comprising repeating unit(s) of the formula

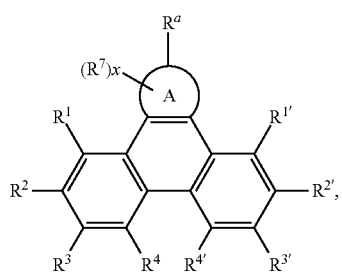

wherein A is a 5-, 6-, or 7-membered heteroaromatic ring, containing at least one heteroatom selected from nitrogen, oxygen and sulfur, especially one nitrogen atom and at least one further heteroatom selected from nitrogen, substituted nitrogen, oxygen and sulfur, at least one of $R^a$, $R^1$, $R^2$, $R^3$, $R^4$, $R^{1'}$, $R^{2'}$, $R^{3'}$ and $R^{4'}$ is a group $R^{10}$, wherein $R^{10}$ is a group $-(Sp)_{x1}-[PG']<$, wherein Sp is a spacer unit, PG' is a group derived from a polymerisable group, x1 is 0, or 1, and x is 0, or an integer of 1 to 4.

WO2008031743 relates electroluminescent devices, comprising a compound of the formula

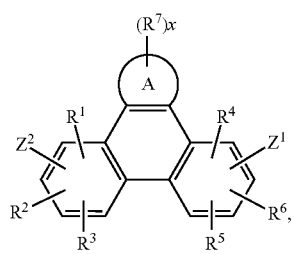

especially as host for phosphorescent compounds. A is a 5-, 6-, or 7-membered heteroaromatic ring, containing at least one heteroatom selected from nitrogen, oxygen and sulfur, especially one nitrogen atom and at least one further heteroatom selected from nitrogen, substituted nitrogen, oxygen and sulfur.

WO2008/119666 discloses compounds of the formula

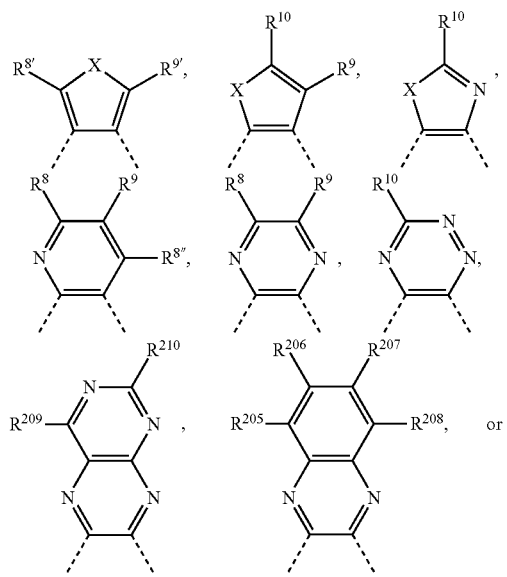

a process for their preparation and their use in organic light emitting diodes (OLEDs), especially as host for phosphorescent compounds. A is a 5-, 6-, or 7-membered heteroaromatic ring, containing at least one heteroatom selected from nitrogen, oxygen and sulfur, especially one nitrogen atom and at least one further heteroatom selected from nitrogen, substituted nitrogen, oxygen and sulfur.

Examples of A are:

-continued

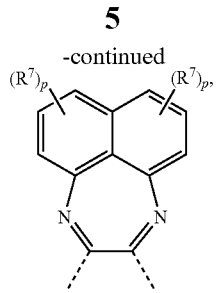

wherein $R^{7'}$ has the meaning of $R^8$, $R^{8'''}$ has the meaning of $R^8$, X is O, S, N—$R^{17}$, wherein $R^{205}$, $R^{206}$, $R^{207}$, $R^{208}$, $R^{209}$, $R^{210}$, $R^8$, $R^9$, $R^{8'}$, $R^{9'}$, $R^{10}$ and $R^{17}$ are as defined below, p is 0, 1, 2, or 3 and the dotted line - - - indicates the bonding to the biphenyl unit.

Notwithstanding these developments, there remains a need for organic light emitting devices comprising new host and transport materials to provide improved efficiency, stability, manufacturability, and/or spectral characteristics of electroluminescent devices.

Accordingly, it was the object of the present invention to provide compounds, which when used in organic electronic devices, especially organic light emitting devices showing good efficiencies, good operative lifetimes, good manufacturability, good spectral characteristics, a high stability to thermal stress, and/or a low operating voltage.

Said object has been solved by compounds of the formula

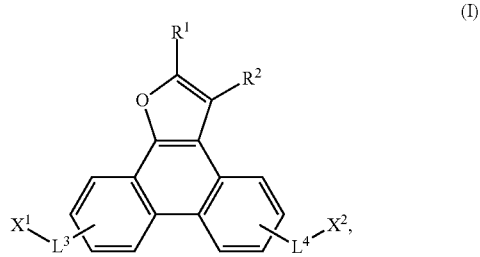

(I)

wherein
$R^1$ and $R^2$ are independently of each other H, F, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or
$R^1$ and $R^2$ form together a group

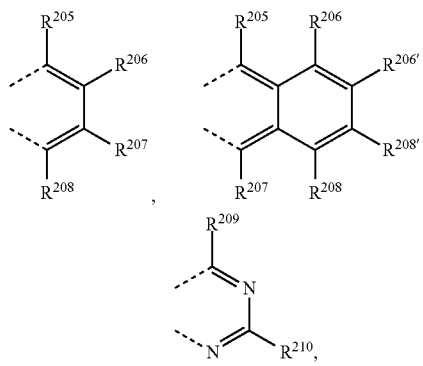

wherein
$R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$fluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, $C_7$-$C_{25}$aralkyl which is substituted by G; CN, or —CO—$R^{28}$, $X^1$ and $X^2$ are independently of each other a group -$NA^1A^{1'}$, $A^1$ and $A^{1'}$ are independently of each other a $C_6$-$C_{24}$aryl group, a $C_6$-$C_{24}$aryl group, which is substituted by G; a $C_2$-$C_{20}$heteroaryl group, or a $C_2$-$C_{20}$heteroaryl group which is substituted by G; or $A^1$ and $A^{1'}$ together with the nitrogen atom to which they are bonded form a heteroaromatic ring, or ring system, such as

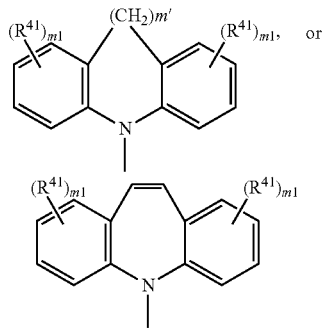

(= group I); m' is 0, 1, or 2; a $C_{10}$-$C_{28}$aryl group (= group III), which can optionally be substituted by G; and/or -$L^3$-$X^1$ and -$L^4$-$X^2$ are independently of each other a group of formula

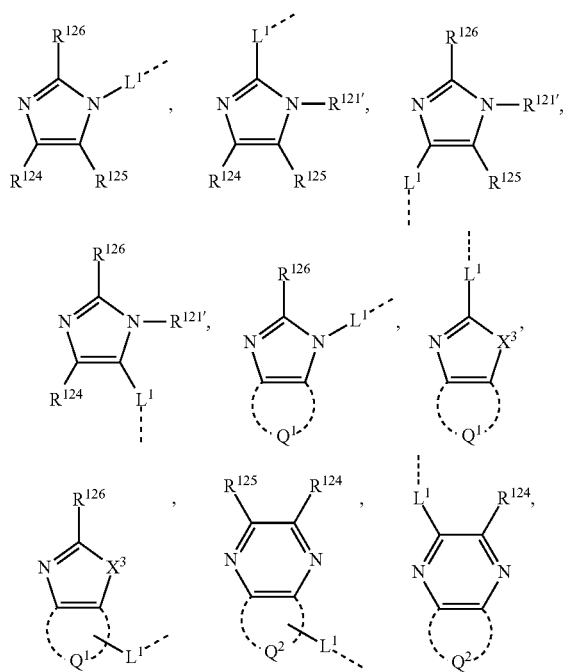

(= group II); wherein

R$^{5''}$, R$^{6''}$, R$^{7''}$, and R$^{8''}$ are independently of each other C$_6$-C$_{18}$aryl; which may optionally be substituted by G; or C$_2$-C$_{20}$heteroaryl, which may optionally be substituted by G, R$^{9''}$ is hydrogen, or has the meaning of R$^{5''}$, m6 is an integer of 1 to 4, X$^3$ represents O, S or N—R$^{121'}$, especially N—R$^{121'}$, X$^9$ represents O, S or N—R$^{121'}$, especially O, Q$^1$ and Q$^2$ represents atoms necessary for forming a carbocyclic aromatic, or heterocyclic aromatic ring, which can optionally be condensed with other ring(s) to form a condensed ring, and/or can optionally be substituted by G, R$^{116}$ and R$^{117}$ are independently of each other H, halogen, —CN, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, C$_7$-C$_{25}$aralkyl, which is substituted by G; —C(=O)—R$^{78}$, —C(=O)OR$^{77}$, or —C(=O)NR$^{75}$R$^{76}$, or substituents R$^{116}$, R$^{117}$ and R$^{117'}$, which are adjacent to each other, can form a ring, R$^{75}$, R$^{76}$ and R$^{78}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{77}$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{121'}$ is C$_6$-C$_{18}$aryl; or C$_2$-C$_{20}$heteroaryl; which can optionally be substituted by C$_1$-C$_{18}$alkyl, C$_1$-C$_{18}$-fluoroalkyl, or C$_1$-C$_{18}$alkoxy; C$_1$-C$_{18}$alkyl; or C$_1$-C$_{18}$alkyl which is interrupted by —O—;

R$^{123}$, R$^{124}$, R$^{125}$ and R$^{126}$ are independently of each other H, C$_1$-C$_{18}$alkyl, C$_1$-C$_{18}$alkyl which is substituted by E and/or interrupted by D, C$_1$-C$_{18}$-fluoroalkyl, C$_6$-C$_{24}$aryl, which can optionally be substituted by G, C$_2$-C$_{20}$heteroaryl, which can optionally be substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, R$^{127}$ and R$^{128}$ are independently of each other H, CN, C$_1$-C$_{18}$alkyl, C$_1$-C$_{18}$alkyl which is substituted by E and/or interrupted by D, C$_1$-C$_{18}$-fluoroalkyl, C$_6$-C$_{24}$aryl, which can optionally be substituted by G, C$_2$-C$_{20}$heteroaryl, which can optionally be substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, L$^1$ is a single bond, —(CR$^{47}$=CR$^{48}$)$_{m2}$—, —(Ar$^3$)$_{m3}$—, —[Ar$^3$(Y$^1$)$_{m5}$]$_{m4}$—, —[(Y$^1$)$_{m5}$Ar$^3$]$_{m4}$—, or —[Ar$^3$(Y$^2$)$_{m5}$Ar$^4$]$_{m4}$—, wherein Y$^1$ is —(CR$^{47}$=CR$^{48}$)—, Y$^2$ is NR$^{49}$, O, S, C=O, C(=O)O, wherein R$^{49}$ is H; C$_6$-C$_{18}$aryl which can optionally be substituted by C$_1$-C$_{18}$alkyl, or C$_1$-C$_{18}$alkoxy; C$_1$-C$_{18}$alkyl; or C$_1$-C$_{18}$alkyl which is interrupted by —O—;

R$^{47}$ and R$^{48}$ are independently of each other hydrogen, fluorine, C$_1$-C$_{25}$alkyl, or C$_6$-C$_{24}$aryl, which can optionally be substituted by G, m2 is an integer of 1 to 10, m3 is an integer of 1 to 5, m4 is an integer of 1 to 5, m5 is an integer of 1 to 10, Ar$^1$ and A$^2$ are independently of each other C$_6$-C$_{24}$aryl, which can optionally be substituted by G, or C$_2$-C$_{20}$heteroaryl, which can optionally be substituted by G, Ar$^3$ and Ar$^4$ are independently of each other arylen, or heteroarylen, which can optionally be substituted.

X$^4$, X$^5$ and X$^6$ are independently of each other N, or CH, with the proviso that at least one, preferably at least two of the substituents X$^4$, X$^5$ and X$^6$ are N, and L$^3$ and L$^4$ are independently of each other a single bond, or a bridging unit BU, such as

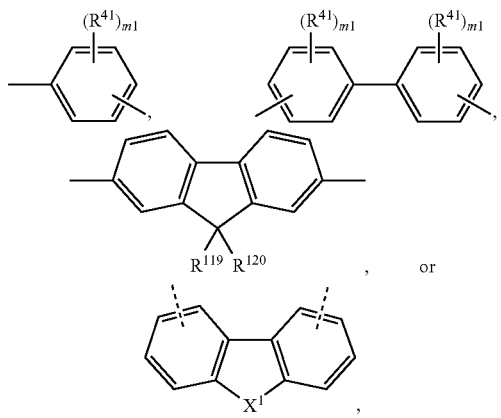

R$^{41}$ can be the same or different at each occurrence and is Cl, F, CN, NR$^{45}$R$^{45'}$, a C$_1$-C$_{25}$alkyl group, a C$_4$-C$_{18}$cycloalkyl group, a C$_1$-C$_{25}$alkoxy group, in which one or more carbon atoms which are not in neighbourhood to each other could be replaced by —NR$^{45}$—, —O—, —S—, —C(=O)—O—, or —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, or two or more groups R$^{41}$ form a ring system;

X$^1$ is O, S, or NR$^{43}$;

R$^{43}$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—; or C$_2$-C$_{20}$heteroaryl group;

$R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein $R^{121}$ and $R^{122}$ are independently of each other H, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{28}$, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —SO$_2$—, —O—, —N$R^{65}$—, —Si$R^{70}R^{71}$—, —PO$R^{72}$—, —$CR^{63}$=$CR^{64}$—, or —C≡C—, and E is —O$R^{69}$, —S$R^{69}$, —N$R^{65}R^{66}$, —CO$R^{68}$, —COO$R^{67}$, —CON$R^{65}R^{66}$, —CN, or halogen, G is E, or $C_1$-$C_{18}$alkyl, $R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl;

$R^{45}$ and $R^{45'}$ are independently of each other a $C_1$-$C_{25}$alkyl group, a $C_4$-$C_{18}$cycloalkyl group, in which one or more carbon atoms which are not in neighbourhood to each other could be replaced by —N$R^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, $R^{45''}$ is a $C_1$-$C_{25}$alkyl group, or a $C_4$-$C_{18}$cycloalkyl group, and m1 can be the same or different at each occurrence and is 0, 1, 2, 3, or 4, especially 0, 1, or 2, very especially 0 or 1.

Among the groups of formula

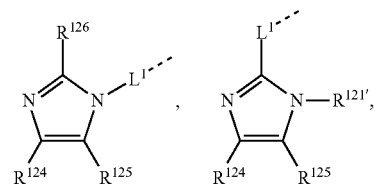,

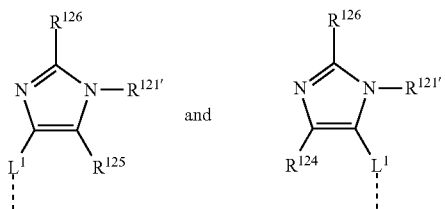 and the groups of formula

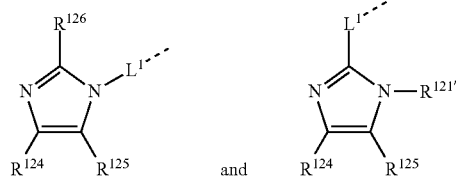 and are preferred.

Compounds of formula

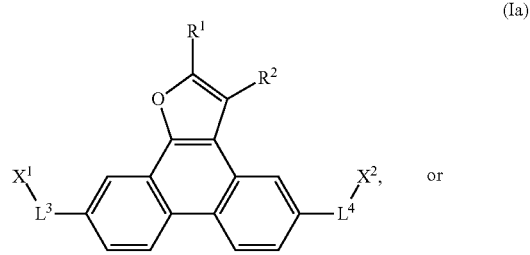 or

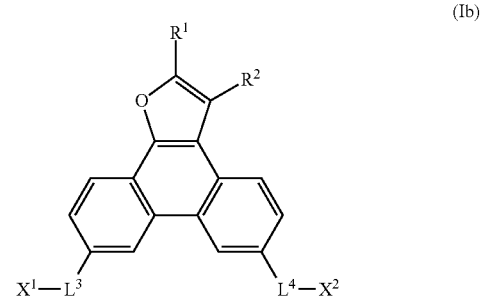

are preferred wherein $X^1$, $X^2$, $L^3$, $L^4$, $R^1$ and $R^2$ are as defined above.

Preferably, $R^1$ and $R^2$ are a group of formula

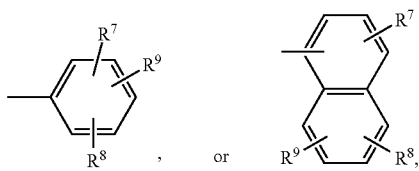

wherein $R^7$, $R^8$ and $R^9$ are independently of each other H, $C_1$-$C_{18}$alkyl, $C_1$-$C_{18}$alkoxy, or $C_1$-$C_{18}$alkyl which is interrupted by O; or $R^1$ and $R^2$ form together a group

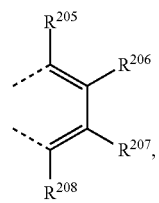

wherein $R^{205}$, $R^{206}$, $R^{207}$, and $R^{208}$ are independently of each other H, $C_1$-$C_{18}$alkyl, $C_1$-$C_{18}$alkyl which is interrupted by O, $C_1$-$C_{18}$alkoxy, or $C_1$-$C_{18}$alkoxy which is interrupted by O, or $C_1$-$C_{18}$fluoroalkyl.

$L^1$, $L^3$ and $L^4$ are independently of each other a single bond, or a bridging unit BU. Examples of the bridging unit BU are groups of formula

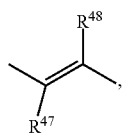

especially

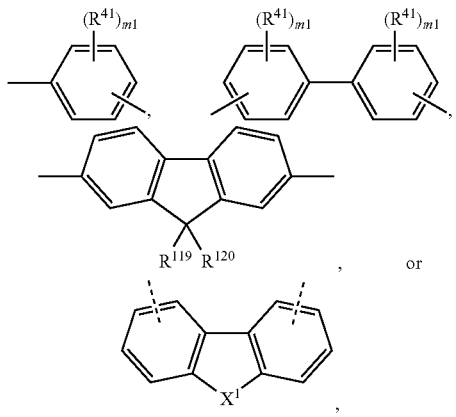

wherein $m^1$, $X^1$, $R^{41}$, $R^{119}$ and $R^{120}$ are as defined above and $R^{47}$ and $R^{48}$ are independently of each other H, $C_1$-$C_{18}$alkyl, or $C_6$-$C_{10}$aryl, which may optionally be substituted by one, or more $C_1$-$C_8$alkyl, or $C_1$-$C_8$alkoxy groups.

Preferably, $R^{119}$ and $R^{120}$ are independently of each other $C_1$-$C_{12}$alkyl, such as methyl, ethyl, n-propyl, iso-propyl, n-butyl, sec-butyl, hexyl, octyl, or 2-ethyl-hexyl, $C_1$-$C_{12}$alkyl which is substituted by E and/or interrupted by D, such as —$CH_2(OCH_2CH_2)_wOCH_3$, w=1, 2, 3, or 4, $C_6$-$C_{14}$aryl, such as phenyl, naphthyl, or biphenylyl, $C_6$-$C_{14}$aryl which is substituted by G, such as —$C_6H_4OCH_3$, —$C_6H_4OCH_2CH_3$, —$C_6H_3(OCH_3)_2$, —$C_6H_3(OCH_2CH_3)_2$, —$C_6H_4CH_3$, —$C_6H_3(CH_3)_2$, —$C_6H_2(CH_3)_3$, or —$C_6H_4tBu$, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl.

Preferably, m1 is 0, or 1.

Preferably, $R^{41}$ is $C_1$-$C_{12}$alkyl, $C_1$-$C_{12}$alkyl which is substituted interrupted by O, or $C_1$-$C_{12}$alkoxy.

Preferably, $R^{47}$ and $R^{48}$ are independently of each other H, or $C_1$-$C_4$alkyl.

Most preferred $L^1$, $L^3$ and $L^4$ are a single bond, or a group

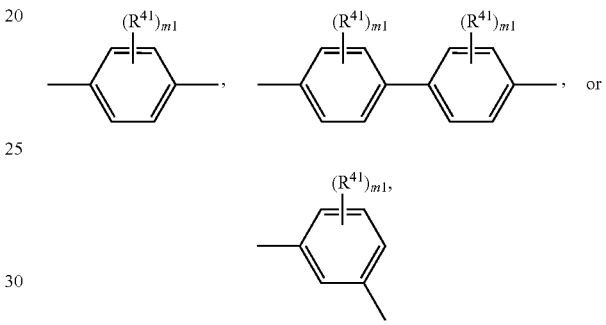

wherein m1 is 0, or 1, and $R^{41}$ is a $C_1$-$C_{25}$alkyl group.

In a preferred embodiment of the present invention -$L^3$-$X^1$ and -$L^4$-$X^2$ are independently of each other a group of formula -$NA^1A^{1'}$, or a group

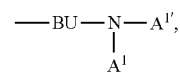

wherein $A^1$ and $A^{1'}$ are independently of each other

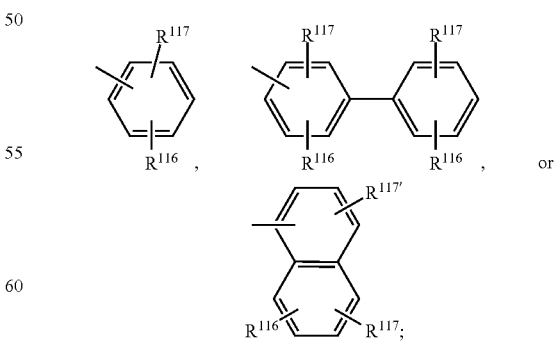

or $A^1$ and $A^{1'}$ together with the nitrogen atom to which they are bonded form a heteroaromatic ring, or ring system

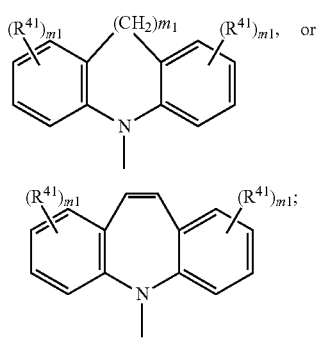

m' is 0, 1, or 2;
m1 can be the same or different at each occurrence and is 0, 1, 2, 3, or 4, especially 0, 1, or 2, very especially 0 or 1;
$R^{116}$, $R^{117}$ and $R^{117'}$ are independently of each other H, halogen, especially F, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{77}$, —C(=O)O$R^{78}$, or —C(=O)N$R^{75}R^{76}$, or substituents $R^{116}$, $R^{117}$ and $R^{117'}$, which are adjacent to each other, can form a ring,
$R^{75}$, $R^{76}$ and $R^{78}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
$R^{77}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
BU is

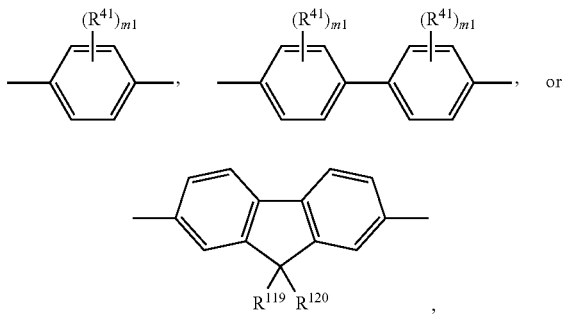

wherein $R^{119}$ and $R^{120}$, m1 and $R^{41}$ is as defined above and m1 is as defined above.

In said embodiment -$L^3$-$X^1$ and -$L^4$-$X^2$ are more preferably independently of each other a group of formula -NA$^1$A$^{1'}$, or a group

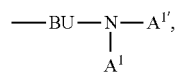

wherein
A$^1$ and A$^{1'}$ are independently of each other

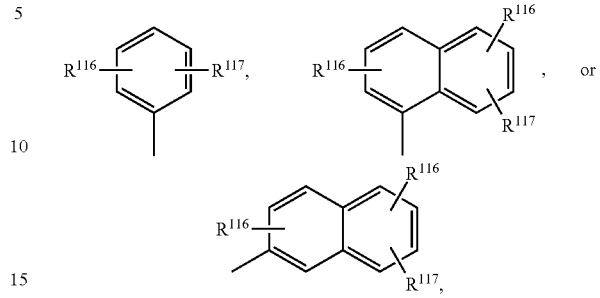

or A$^1$ and A$^{1'}$ together with the nitrogen atom to which they are bonded form a group of formula

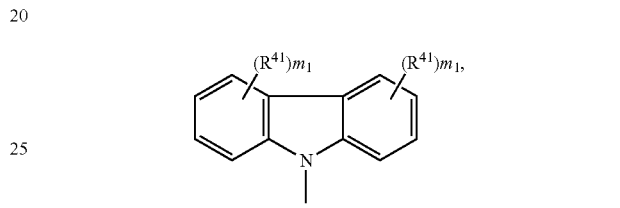

$R^{116}$ and $R^{117}$ are independently of each other $C_1$-$C_{18}$alkyl, which may optionally be interrupted by —O—, or $C_1$-$C_{18}$alkoxy;
Bu is

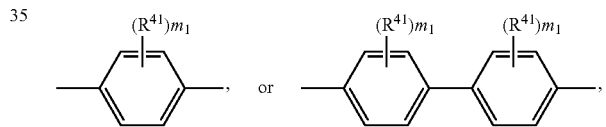

wherein $R^{41}$ can be the same or different at each occurrence and is $C_1$-$C_{25}$alkyl, which may optionally be interrupted by —O—, or $C_1$-$C_{25}$alkoxy; m1 is 0, 1, or 2.

In a further preferred embodiment of the present invention -$L^3$-$X^1$ and -$L^4$-$X^2$ are independently of each other a $C_{10}$-$C_{28}$aryl group, especially a group of formula

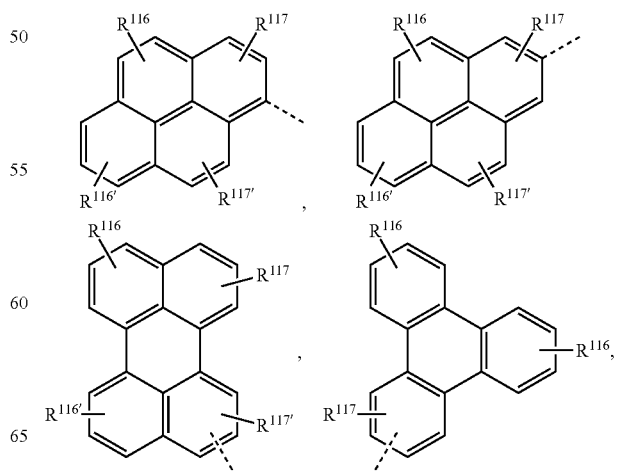

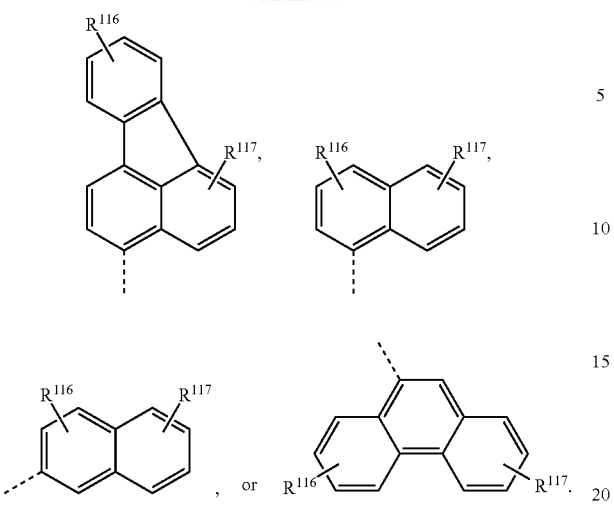

wherein
$R^{116'}$ has the meaning of $R^{116}$, $R^{116'}$, $R^{117}$ and $R^{117'}$ are as defined above, D, E and G are as defined above.

Preferably, $R^{116}$, $R^{116'}$, $R^{117}$ and $R^{117'}$ are independently of each other H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{12}$alkyl which is interrupted by O, such as —$CH_2OCH_3$, —$CH_2OCH_2CH_3$, —$CH_2OCH_2CH_2OCH_3$, or —$CH_2OCH_2CH_2OCH_2CH_3$; or $C_1$-$C_{12}$alkoxy.

In said embodiment -$L^3$-$X^1$ and -$L^4$-$X^2$ are more preferably independently of each other a group of formula

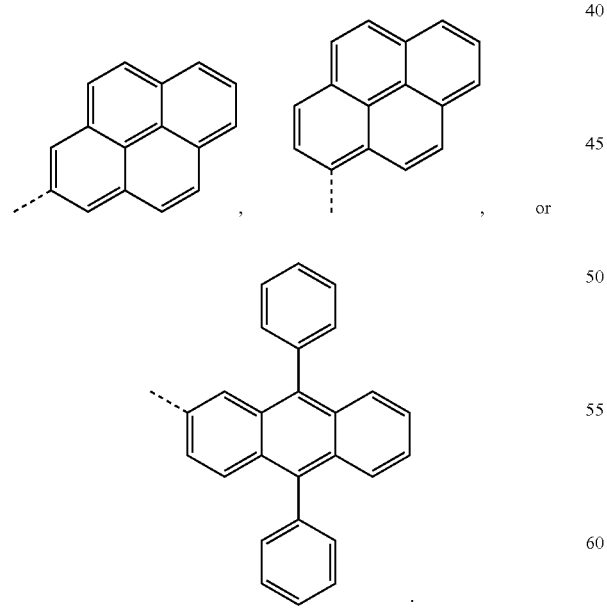

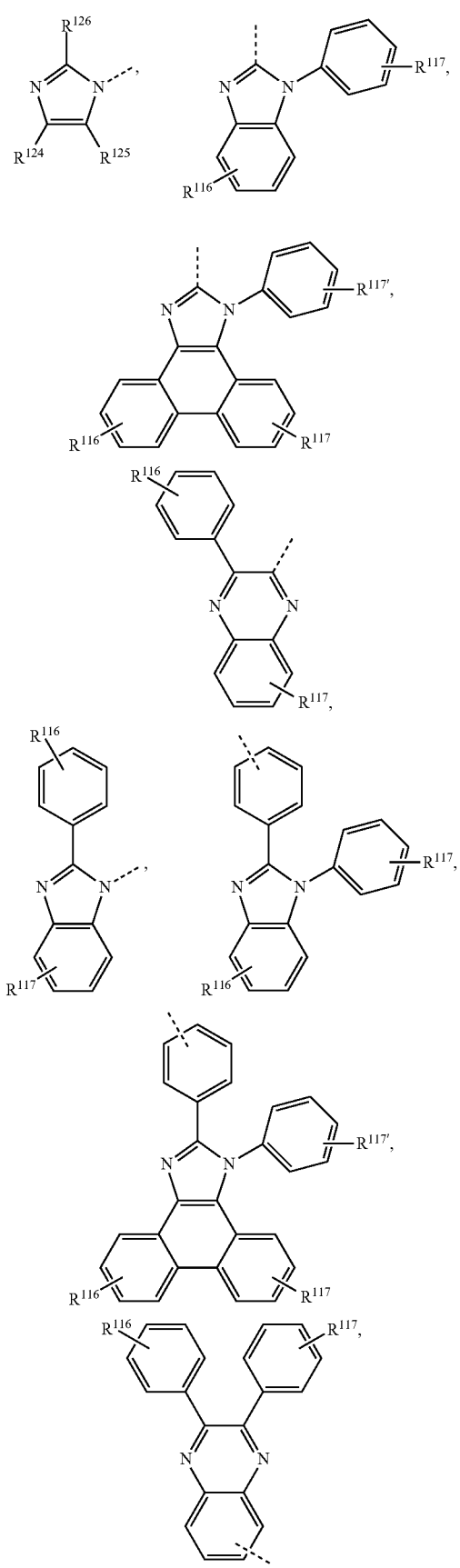

In a further preferred embodiment of the present invention -$L^3$-$X^1$ and -$L^4$-$X^2$ are independently of each other a group of formula

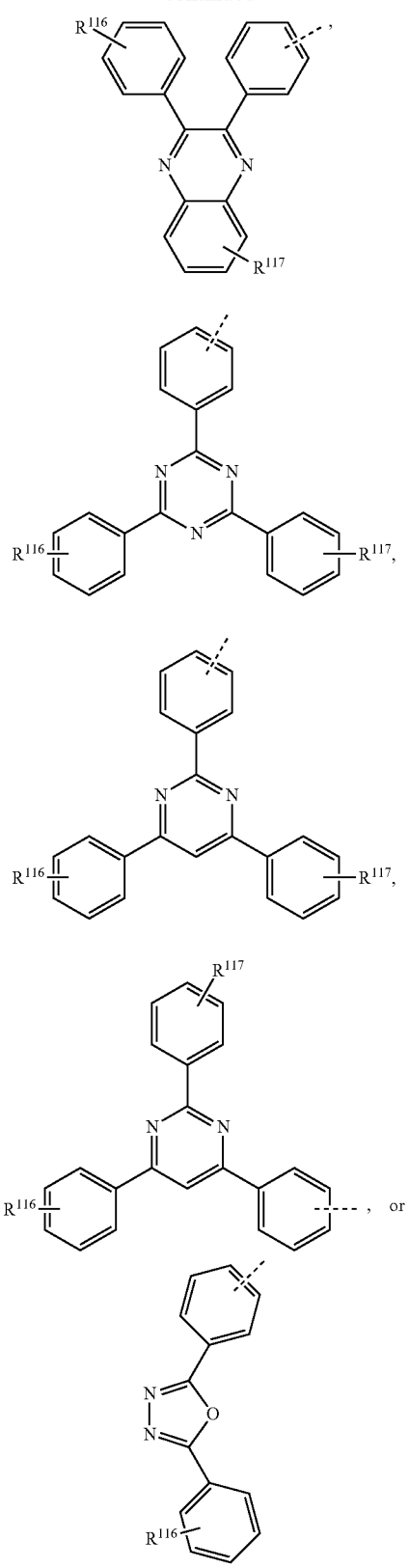

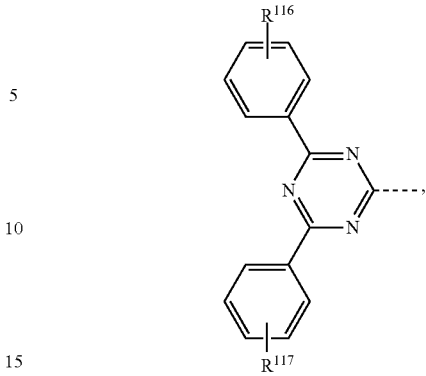

wherein $R^{116}$ and $R^{117}$ are as defined above.

Preferably, $R^{116}$, $R^{116'}$, $R^{117}$ and $R^{117'}$ are independently of each other H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{12}$alkyl which is interrupted by O, such as —$CH_2OCH_3$, —$CH_2OCH_2CH_3$, —$CH_2OCH_2CH_2OCH_3$, or —$CH_2OCH_2CH_2OCH_2CH_3$; or $C_1$-$C_{12}$alkoxy.

In said embodiment -$L^3$-$X^1$ and -$L^4$-$X^2$ are more preferably independently of each other a group of formula

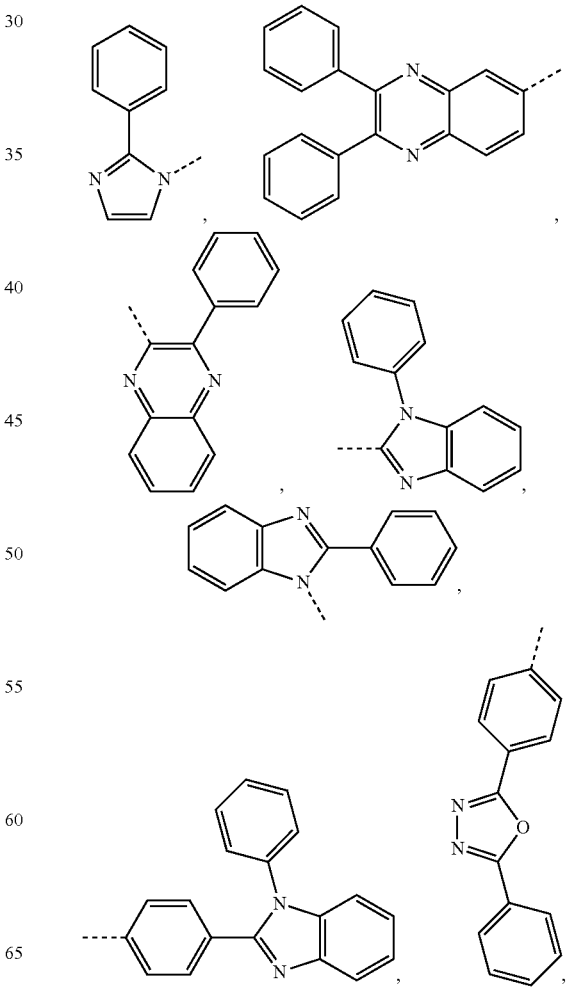

wherein $R^{116}$, $R^{117}$, $R^{117'}$, $R^{124}$, $R^{125}$ and $R^{126}$ are as defined above. In a further preferred embodiment of the present invention -$L^3$-$X^1$ and -$L^4$-$X^2$ are a group of formula -continued

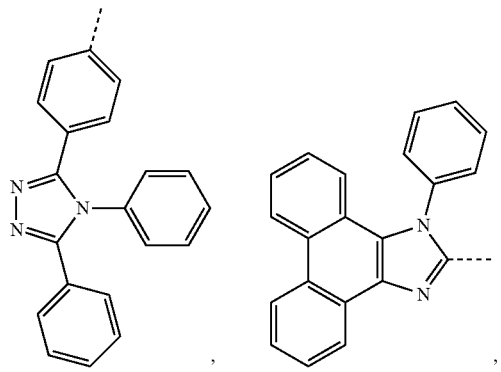, or

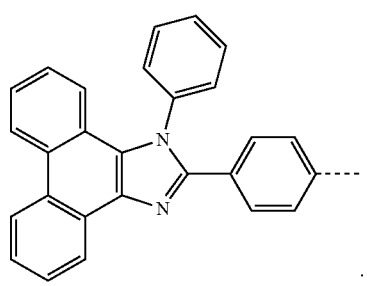.

Alternatively -L³-X¹ and -L⁴-X² are a group of formula

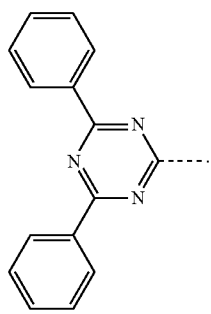

In a particularly preferred embodiment the preent invention is directed to compounds of formula

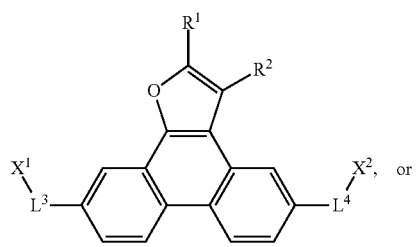
(Ia)

-continued

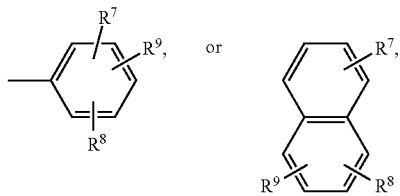
(Ib)

wherein R¹ and R² are a group of formula

wherein $R^7$, $R^8$ and $R^9$ are independently of each other H, $C_1$-$C_{18}$alkyl, $C_1$-$C_{18}$alkoxy, or $C_1$-$C_{18}$alkyl which is interrupted by O; or $R^1$ and $R^2$ form together a group

,

-L³-X¹ and -L⁴-X² are independently of each other a group of formula

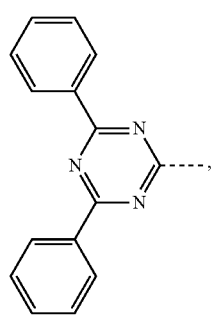

especially

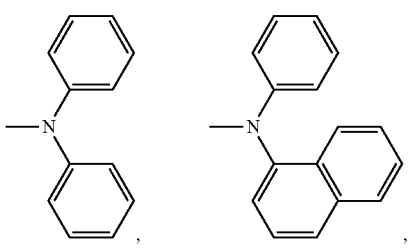,

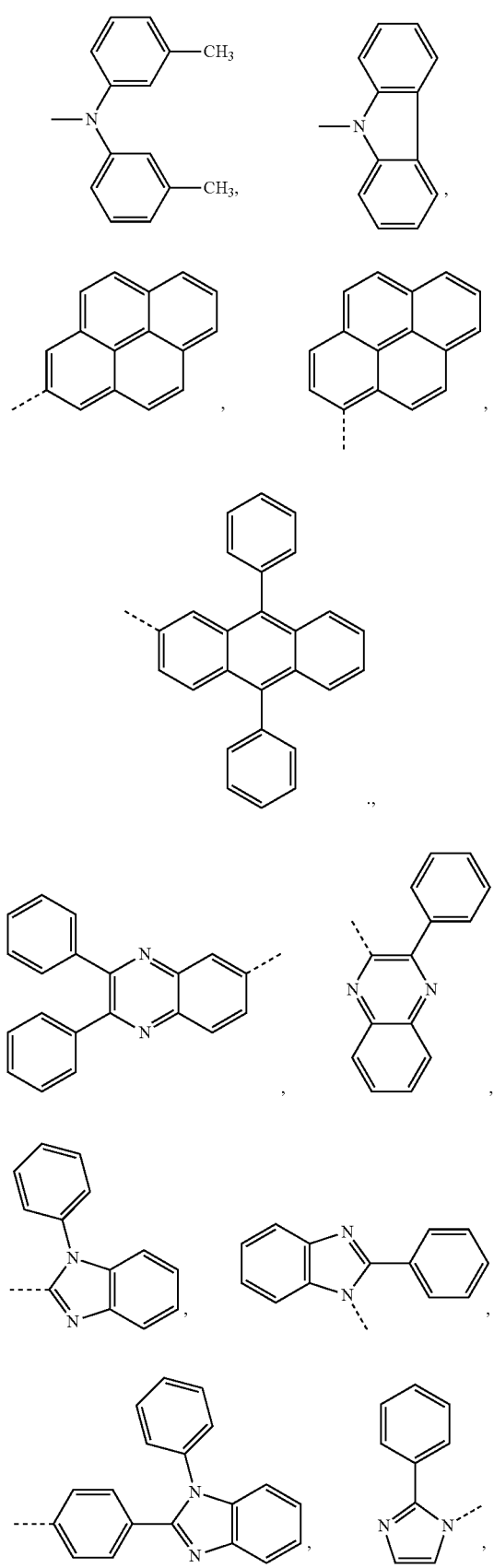
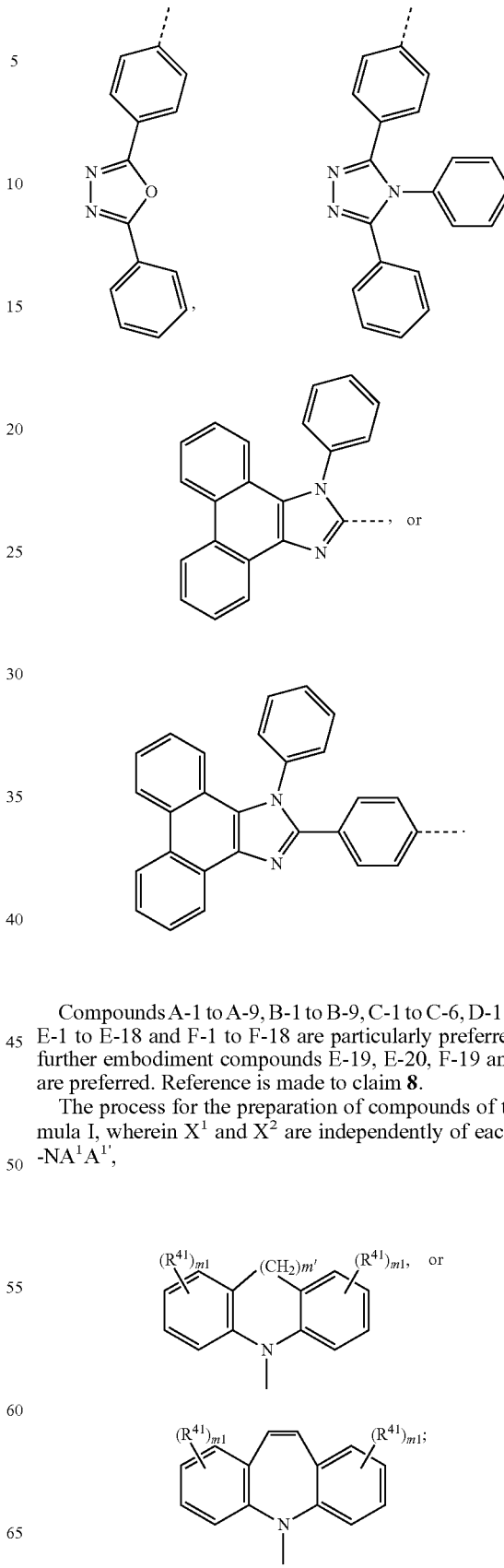
Compounds A-1 to A-9, B-1 to B-9, C-1 to C-6, D-1 to D-6, E-1 to E-18 and F-1 to F-18 are particularly preferred. In a further embodiment compounds E-19, E-20, F-19 and F-20 are preferred. Reference is made to claim 8.
The process for the preparation of compounds of the formula I, wherein $X^1$ and $X^2$ are independently of each other $-NA^1A^{1'}$, m' is 0, 1, or 2; comprises reacting a compound of formula

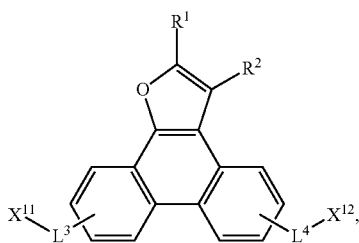
(II)

wherein $X^{11}$ and $X^{12}$ stand for halogen, such as bromo, or iodo,
with a compound of formula $HNA^1A^{1'}$,

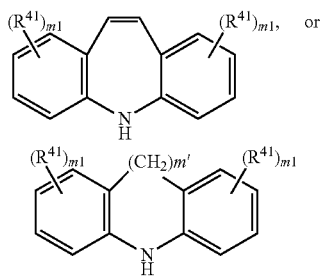

in the presence of a base, such as, for example, sodium hydride, potassium carbonate, or sodium carbonate, and a catalyst, such as, for example, copper (0) or copper (I) (such as copper, copper-bronze, copper bromide iodide, or copper bromide), in a solvent, such as, for example, toluene, dimethyl formamide, or dimethyl sulfoxide, wherein $A^1$, $A^{1'}$, $L^3$, $L^4$, $R^1$, $R^2$, $R^{41}$ and m1 are as defined above.

This reaction, referred to as an Ullmann condensation, is described by Yamamoto & Kurata, Chem. and Industry, 737-738 (1981), J. Mater. Chem. 14 (2004) 2516, H. B. Goodbrand et al., J. Org. Chem. 64 (1999) 670 and K. D. Belfield et al., J. Org. Chem. 65 (2000) 4475 using copper as catalyst. Additionally palladium catalysts can be used for the coupling of aryl halogen compounds with amines, as described in M. D. Charles et al., Organic Lett. 7 (2005) 3965, A. F. Littke et. al., Angew. Chem. Int. Ed. 41 (2002) 4176 and literature cited therein.

The compounds of formula I of the present invention can be prepared according to a process, which comprises reacting a derivative of formula

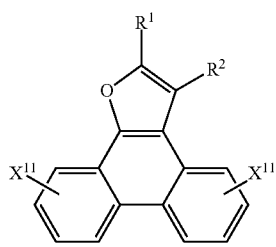

with boronic acid derivative $X^{12}$—Ar; or reacting a derivative of formula

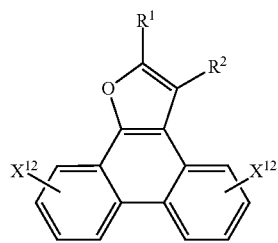

with $X^{11}$—Ar; wherein
$X^{11}$ stands for halogen such as chloro or bromo, or iodo, preferably bromo, or iodo, most preferably bromo, $X^{12}$ having the meaning of
—$B(OH)_2$, —$B(OY^1)_2$,

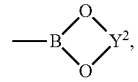

—$BF_4Na$, or —$BF_4K$,
Ar is a group of formula

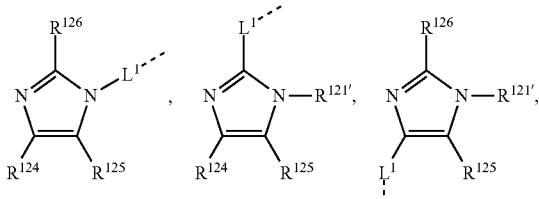

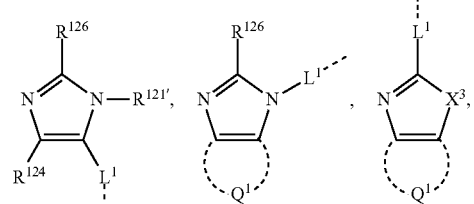

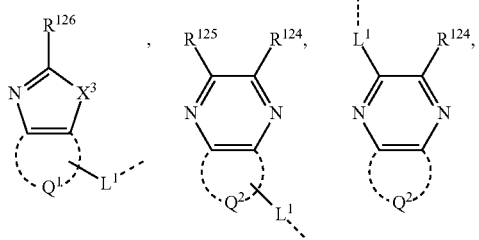

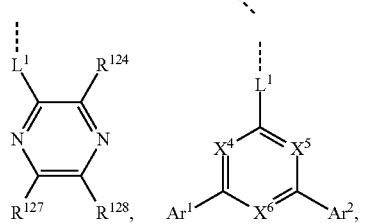

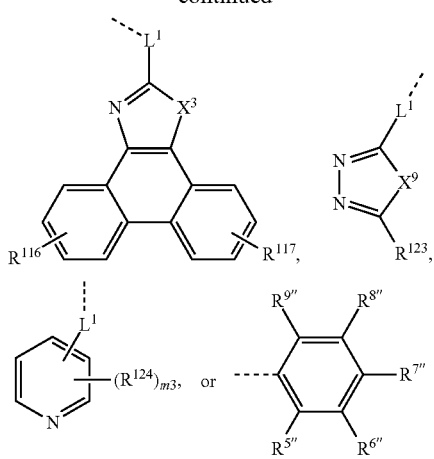

(= group II); or a $C_{10}$-$C_{28}$ aryl group (= group III), in the presence of an allylpalladium catalyst of the μ-halo (triisopropylphosphine)($\eta^3$-allyl)palladium(II) type (see for example WO99/47474).

Preferably, the reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, $Na_2CO_3$, $K_2CO_3$, $Cs_2CO_3$ and the like, preferably an aqueous $K_2CO_3$ solution is chosen. Usually, the molar ratio of the base to boronic acid or boronic ester derivative is chosen in the range of from 0.5:1 to 50:1, very especially 1:1. Generally, the reaction temperature is chosen in the range of from 40 to 180° C., preferably under reflux conditions. Preferred, the reaction time is chosen in the range of from 1 to 80 hours, more preferably from 20 to 72 hours. In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as $PdAc_2$ or $Pd_2 dba_3$ and to the addition of ligands selected from the group consisting of

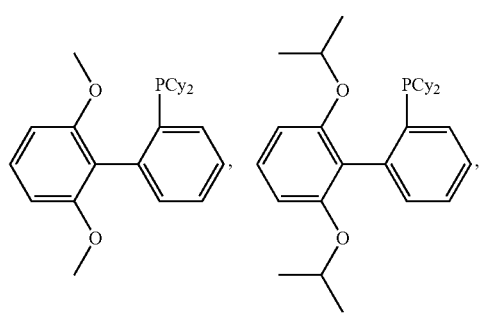

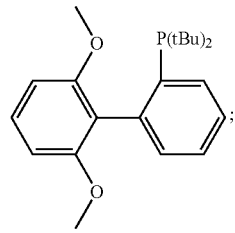

wherein Cy=

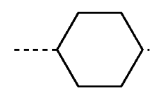

The ligand is added in a ratio of from 1:1 to 1:10, based on Pd. Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 per mol of boronic acid derivative.

Compounds of formula I, wherein -$L^3$-$X^1$ and -$L^4$-$X^2$ are identical and are a group of formula

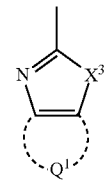

can be prepared according to, or in analogy to Synthesis 2005, 47 or Synthesis; 2003, 1683. An example of such a reaction is shown below:

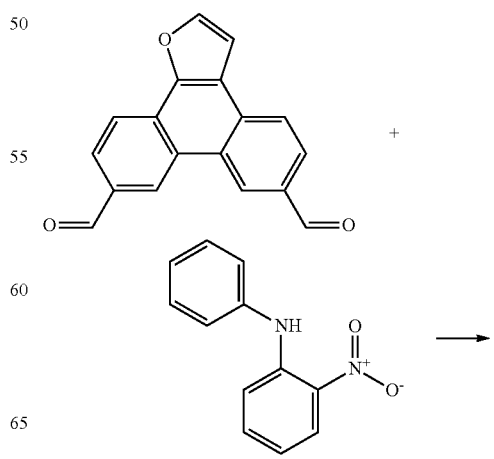

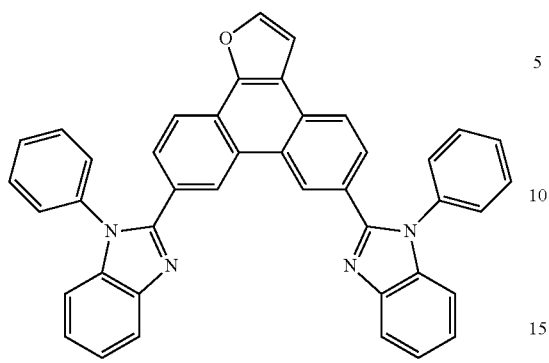

Compounds of formula I, wherein -L³-X¹ and -L⁴-X² are identical and are a group of formula

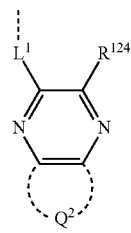

can be prepared according to, or in analogy to Adv. Funkt. Mater. 2006, 16, 1449. An example of such a reaction is shown below:

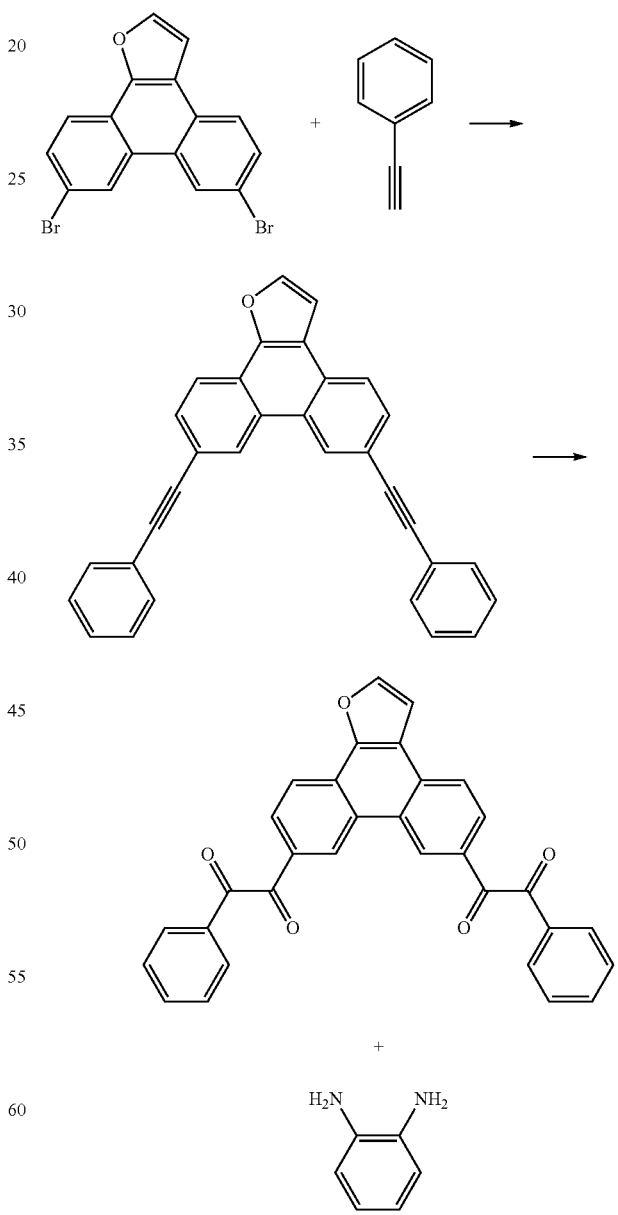

can be prepared (Ulmann reaction) according, or in analogy to Inorg. Chem. 2006, 45, 147, or Inorg. Chem. 2005, 44, 1232.

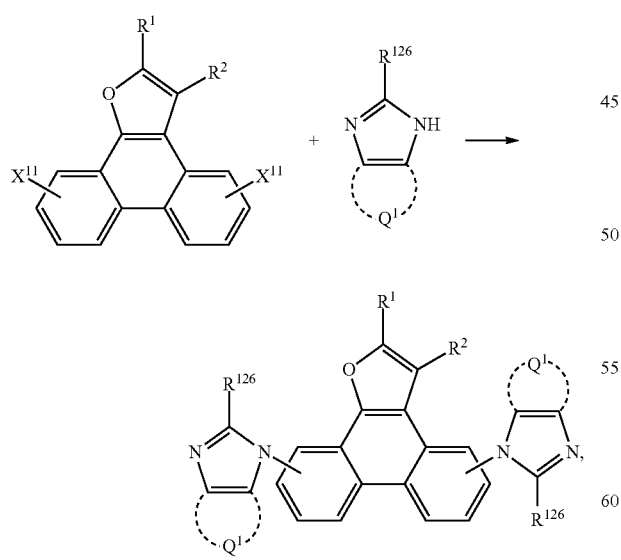

wherein $X^{11}$ stands for bromo, or iodo, preferably iodo.

Compounds of formula I, wherein -L³-X¹ and -L⁴-X² are identical and are a group of formula

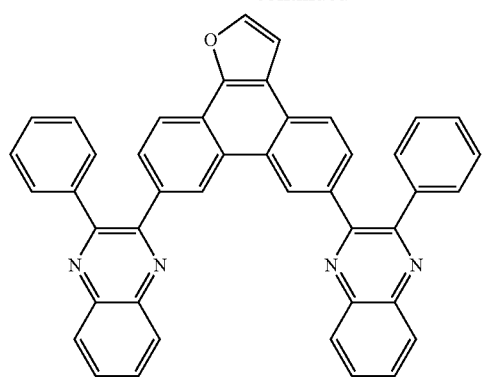

Compounds of the formula

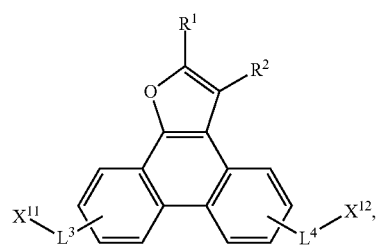 (II)

wherein $L^3$, $L^4$, $R^1$ and $R^2$ are as defined in claim 1;

$X^{11}$ and $X^{12}$ are independently in each occurrence a halogen atom, or —OS(O)$_2$CF$_3$, —OS(O)$_2$-aryl, especially

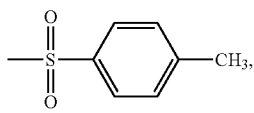

—OS(O)$_2$CH$_3$, —B(OH)$_2$, —B(OY$^1$)$_2$,

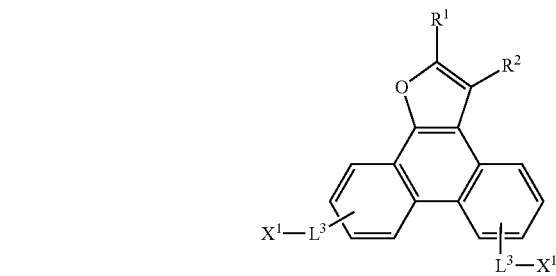

—BF$_4$Nla, or —BF$_4$K, wherein $Y^1$ is independently in each occurrence a C$_1$-C$_{10}$alkyl group and $Y^2$ is independently in each occurrence a C$_2$-C$_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a C$_1$-C$_{10}$alkyl group, especially —C(CH$_3$)$_2$C(CH$_3$)$_2$—, —CH$_2$C(CH$_3$)$_2$CH$_2$—, or —C(CH$_3$)$_2$CH$_2$C(CH$_3$)$_2$—, are intermediates in the production of the compounds of formula I and form a further subject of the present invention.

The preparation of phenanthro[9,10-b]furanes can be carried out as described in J. Chem. Soc. Perkin Trans. 1989, 2329; Tetrahedron Letters 1969, 457; J. Chem. Soc. Perkin Trans. 1991, 3159 and J. Chem. Soc. Perkin Trans. 1990, 2127.

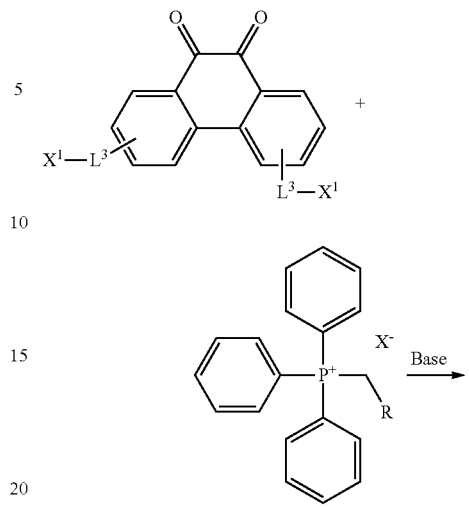

R has the meaning of $R^1$.

Tetrahedron 2010, 66, 5612 describes the synthesis phenanthro[9,10-b]furanes, in which $R^1$ and $R^2$ forms a ring.

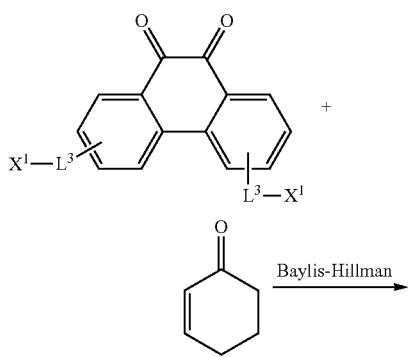

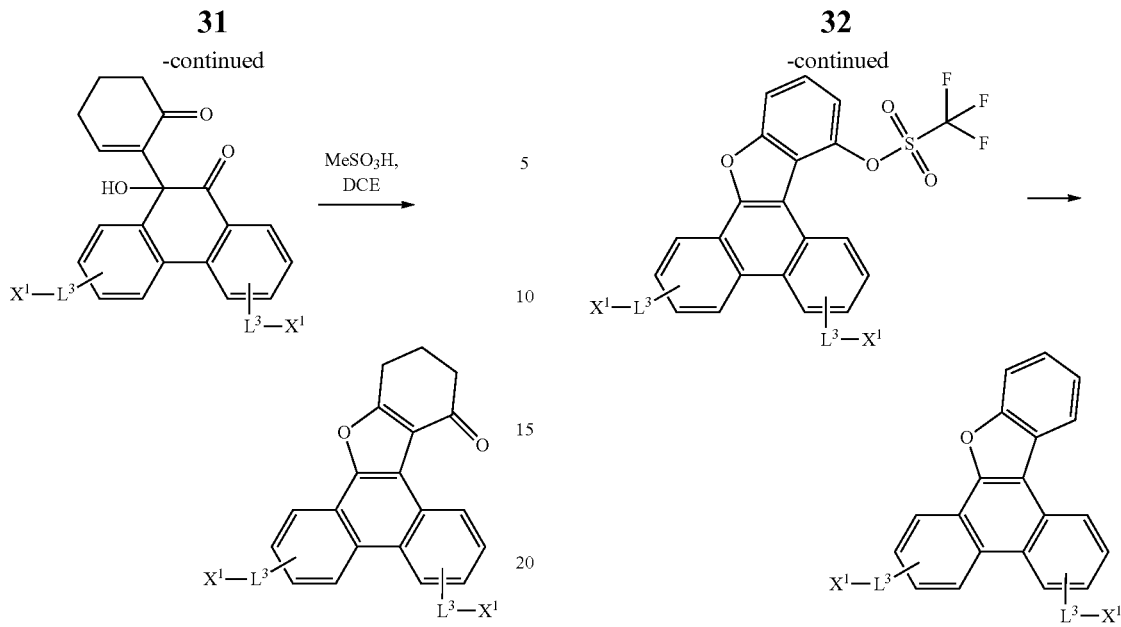

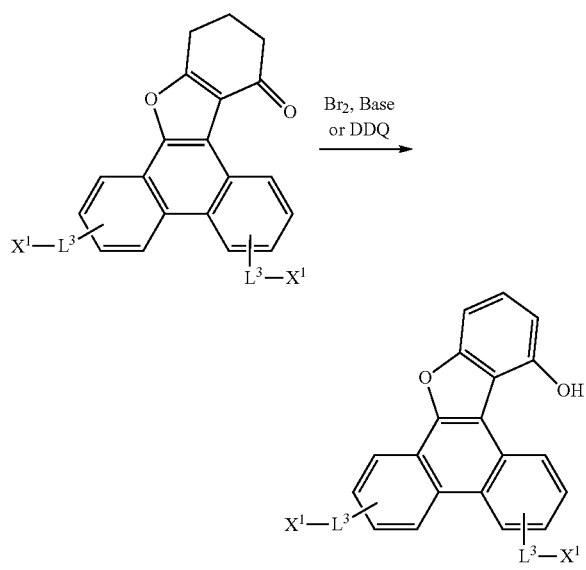

Aromatization of the ring can be achieved according to Synthetic Communications 2006, 36, 1983-1990, or Synthesis 2003, 13, 1977-1988.

The hydroxy group can be removed in analogy to the process described in example 4 and 5 of WO2006000544.

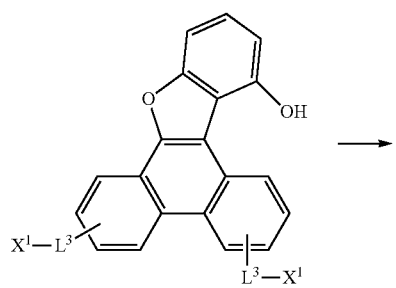

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices (=organic light-emitting diodes (OLEDs)).

Accordingly, a further subject of the present invention is directed to an electronic device, comprising a compound according to the present invention.

The electronic device is preferably an electroluminescent device.

Group I substituted compounds of formula I, such as, for example, A-1 to A-9 and B-1 to B-9, can be used as hole transport materials and/or hosts.

Group II substituted compounds of formula I, such as, for example, C-1 to $C_{1-6}$ and D-1 to D-6, can be used as electron transport materials.

Group III substituted compounds of formula I, such as, for example, E-1 to E-20 and F-1 to F-20, can be used as electron transport materials.

Hence, a further subject of the present invention is directed to a hole transport layer, or an electron transport layer, comprising a compound of the present invention.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_2$-$C_{25}$alkenyl groups ($C_2$-$C_{18}$alkenyl groups) are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_2$-$C_{24}$alkynyl ($C_{2-18}$alkynyl) is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

The term "cycloalkyl group" is typically $C_4$-$C_{18}$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_1$-$C_{18}$fluoroalkyl, especially $C_1$-$C_4$-fluoroalkyl, is a branched or unbranched radical, wherein all, or part of the hydrogen atoms are replaced by F, such as for example —$CF_3$, —$CF_2CF_3$, —$CF_2CF_2CF_3$, —$CF(CF_3)_2$, —$(CF_2)_3$$CF_3$, and —$C(CF_3)_3$.

$C_6$-$C_{24}$aryl, which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

$C_2$-$C_{20}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

The $C_6$-$C_{24}$aryl and $C_2$-$C_{20}$heteroaryl groups are preferably substituted by one, or more $C_1$-$C_8$alkyl groups.

The term "aryl ether group" is typically a $C_{6-24}$aryloxy group, that is to say O—$C_{6-24}$aryl, such as, for example, phenoxy or 4-methoxyphenyl.

The term "aralkyl group" is typically $C_7$-$C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω, ω-dimethyl-ω-phenyl-butyl, in which both the aliphatic hydrocarbon group and aromatic hydrocarbon group may be unsubstituted or substituted.

Examples of arylene radicals are phenylene, naphthylene, phenalenylene, antracylene and phenantrylene, which may optionally be substituted by one or more $C_1$-$C_{18}$alkyl groups. Preferred arylene radicals are 1,3-phenylene, 3,6-naphthylene, and 4,9-phenalenylene, which may optionally be substituted by one or more $C_1$-$C_{18}$alkyl groups.

Examples of heteroarylene radicals are 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene, 2,6-indenylene, especially pyrazinylene, pyridinylene, pyrimidinylene, and triazolylene, which may optionally be substituted by one or more $C_1$-$C_{18}$alkyl groups. Preferred heteroarylene radicals are 2,6-pyrazinylene, 2,6-pyridinylene, 4,6-pyrimidinylene, and 2,6-triazolylene, which may optionally be substituted by one or more $C_1$-$C_{18}$alkyl groups.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group.

The term "haloalkyl" mean groups given by partially or wholly substituting the above-mentioned alkyl group with halogen, such as trifluoromethyl etc.

If a substituent, such as, for example $R^{41}$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(OR$^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR_z$, CH($CH_3$)CO-OR$^z$, C($CH_3$)$_2$COOR$^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2$CH(OH)$CH_2$—O—CO—C($CH_3$)=$CH_2$.

The organic electronic device of the present application is, for example, an organic solar cell (organic photovoltaics), a switching element. such as an organic transistors, for example organic FET and organic TFT, organic light emitting field effect transistor (OLEFET), or an organic light-emitting diode (OLED), preference being given to OLEDs.

The compounds of formula I are preferably used as electron transport materials, hole transport materials and/or hosts for phosphorescent materials.

In an especially preferred embodiment of the present application relates compounds of formula I are used in combination with a phosphorescent emitter preferably as host in an organic light emitting device.

Phosphorescent Materials

Phosphorescent materials may be used alone or, in certain cases, in combination with each other, either in the same or different layers. Examples of phosphorescent and related materials are described in WO00/57676, WO00/70655, WO01/41512, WO02/15645, US2003/0017361, WO01/93642, WO01/39234, U.S. Pat. No. 6,458,475, WO02/071813, U.S. Pat. No. 6,573,651, US2002/0197511, WO02/074015, U.S. Pat. No. 6,451,455, US2003/0072964, US2003/0068528, U.S. Pat. Nos. 6,413,656, 6,515,298, 6,451,415, 6,097,147, US2003/0124381, US2003/0059646, US2003/0054198, EP1239526, EP1238981, EP1244155, US2002/0100906, US2003/0068526, US2003/0068535, JP2003073387, JP2003073388, US2003/0141809, US2003/0040627, JP2003059667, JP2003073665, US2002/0121638, WO06/000544, WO07/074093, WO07/115981, WO08/101842, WO09/100991, WO10/129323, WO2010056669, WO10086089, US2010/213834, US2011/089407, and WO11/073149.

The emission wavelengths of cyclometallated Ir(III) complexes of the type $IrL_3$ and $IrL_2L'$, such as the green-emitting fac-tris(2-phenylpyridinato-$N,C^{2'}$)iridium(III) and bis(2-phenylpyridinato-$N,C^{2'}$)Iridium(III) (acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are bis(1-(phenyl)isoquinoline) iridium (III) acetylanetonate, (acetylanetonato)bis(2,3,5-triphenylpyrazinato) iridium(III), bis(2-(2'-benzothienyl)pyridinato-$N,C^{3'}$)iridium(III)-(acetylacetonate) and tris(1-phenylisoquinolinato-N,C)iridium(III). A blue-emitting example is bis(2-(4,6-difluorophenyl)-pyridinato-$N,C^{2'}$)Iridium(III)(picolinate).

Red electrophosphorescence has been reported, using bis (2-(2'-benzo[4,5-a]thienyl)pyridinato-$N,C^3$)iridium(acetylacetonate)[$Btp_2Ir(acac)$] as the phosphorescent material (Adachi, C., Lamansky, S., Baldo, M. A., Kwong, R. C., Thompson, M. E., and Forrest, S. R., App. Phys. Lett., 78, 1622 1624 (2001)).

Other important phosphorescent materials include cyclometallated Pt(II) complexes such as cis-bis(2-phenylpyridinato-$N,C^{2'}$)platinum(II), cis-bis(2-(2'-thienyl)pyridinato-N, $C^{3'}$) platinum(II), cis-bis(2-(2'-thienyl)quinolinato-$N,C^{5'}$) platinum(II), or (2-(4,6-difluorophenyl)pyridinato-NC2') platinum(II)acetylacetonate. Pt(II)porphyrin complexes such as 2,3,7,8,12,13,17,18-octaethyl-21H,23H-porphine platinum(H) are also useful phosphorescent materials.

Still other examples of useful phosphorescent materials include coordination complexes of the trivalent lanthanides such as $Th^{3+}$ and $Eu^{3+}$ (J. Kido et al, Appl. Phys. Lett., 65, 2124 (1994)).

Other important phosphorescent materials are described in WO06/000544 and WO2008/101842.

Examples of phosphorescent materials are compounds A-1 to A-234, B-1 to B-234, C-1 to C-44 and D-1 to D-234, which are described in WO2008/101842. Preferred examples are described in WO2009/100991 example 48-53 and 54-78.

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell.

The present invention further relates to an organic light-emitting diode comprising an anode An and a cathode Ka, a light-emitting layer E arranged between the anode An and the cathode Ka, an electron transport layer arranged between the cathode Ka and the light-emitting layer E, and if appropriate at least one further layer selected from the group consisting of at least one blocking layer for holes/excitons, at least one blocking layer for electrons/excitons, at least one hole injection layer and at least one hole transport layer.

Structure of the Inventive OLED

The inventive organic light-emitting diode (OLED) thus generally has the following structure:
an anode (An) and a cathode (Ka) and a light-emitting layer E arranged between the anode (An) and the cathode (Ka) and an electron transport layer arranged between the cathode (Ka) and the light-emitting layer E.

The inventive OLED may, for example—in a preferred embodiment—be formed from the following layers:

1. Anode
2. Hole transport layer
3. Light-emitting layer
4. Blocking layer for holes/excitons
5. Electron transport layer
6. Cathode Layer sequences different than the aforementioned structure are also possible, and are known to those skilled in the art. For example, it is possible that the OLED does not have all of the layers mentioned; for example, OLEDs which have layers (1), (3), (4), (5) and (6), are likewise suitable. In addition, the OLEDs may have a blocking layer for electrons/excitons between the hole transport layer (2) and the light-emitting layer (3).

It is additionally possible that a plurality of the aforementioned functions (electron/exciton blocker, hole/exciton blocker, hole injection, hole transport, electron injection, electron transport) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron trans-port layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole transport layer should be matched to the work function of the anode, and the LUMO (lowest unoccupied molecular orbital) of the electron transport layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole transport materials for layer (2) of the inventive OLEDs are disclosed, for example, in Kirk-Othmer Encyclopedia of Chemical Technology, 4th edition, Vol. 18, pages 837 to 860, 1996. Both hole-transport molecules and polymers can be used as the hole transport material. Hole-transport molecules typically used are selected from the group consisting of tris[N-(1-naphthyl)-N-(phenylamino)] triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl] (4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenylamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NP-BAPF), 2,2',7,7'-tetrakis[N-naphthalenyl(phenyl)amino]-9,9'-spirobifluorene (Spiro-2N PB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl)amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole transport materials, the band gap of the at least one hole transport material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is fac-Iridium-tris(1,3-diphenylbenzimidazolin-2-yliden-C,C²') (Ir(dpbic)₃), which is disclosed, for example, in WO2005/019373. Preferably, the hole transport layer comprises a compound of formula

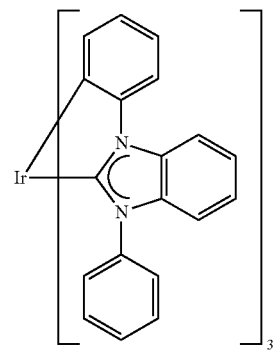

doped with molybdenum oxide ($MoO_x$), especially $MoO_3$, or rhenium oxide ($ReO_x$), especially $ReO_3$. The dopant is contained in an amount of from 0.1% by weight to 60%, preferably 10% to 50% by weight, based on the amount of dopant and carbene complex.

In addition—in one embodiment—it is possible to use Group I substituted compounds of formula I, such as, for example, A-1 to A-9 and B-1 to B-9, as hole transport materials.

The light-emitting layer (3) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981 and WO 2008/000727, WO06/000544, WO07/074093, WO07/115981, WO08/101842, WO09/100991, WO10/129323, WO2010056669, WO10086089, US2010/213834, US2011/089407, and WO11/073149.

In one embodiment of the present invention, the compounds of the formula X are used in the light-emitting layer as matrix material together with carbene complexes as triplet emitters.

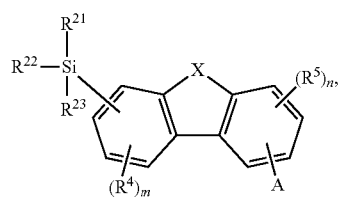

(X)

wherein
X is $NR^{24}$, S, O or $PR^{24}$;
$R^{24}$ is aryl, heteroaryl, alkyl, cycloalkyl, or heterocycloalkyl;
A is $—NR^{26}R^{27}$, $—P(O)R^{28}R^{29}$, $—PR^{10}R^{11}$, $—S(O)_2R^{12}$, $—S(O)R^{13}$, $—SR^{14}$, or $—OR^{15}$;

$R^1$, $R^2$ and $R^3$ are independently of each other aryl, heteroaryl, alkyl, cycloalkyl, or heterocycloalkyl, wherein at least on of the groups $R^1$, $R^2$, or $R^3$ is aryl, or heteroaryl;

$R^4$ and $R^5$ are independently of each other alkyl, cycloalkyl, heterocycloalkyl, aryl, heteroaryl, a group A, or a group having donor, or acceptor characteristics;

n and m are independently of each other 0, 1, 2, or 3;

$R^{26}$, $R^{27}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{28'}$, $R^{29}$, $R^{10}$, $R^{11}$, $R^{12}$, $R^{13}$, $R^{14}$ and $R^{15}$ are independently of each other aryl, heteroaryl, alkyl, cycloalkyl, or heterocycloalkyl. Compounds of formula X, such as, for example,

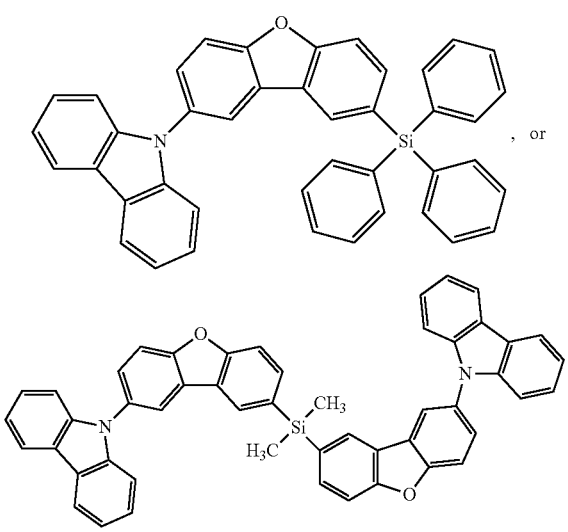

are described in WO2010079051 (PCT/EP2009/067120; in particular pages on 19 to 26 and in tables on pages 27 to 34, pages 35 to 37 and pages 42 to 43).

Additional matrix materials on basis of dibenzofurane are, for example, described in US2009066226, EP1885818B1, EP1970976, EP1998388 and EP2034538. Examples of particularly preferred matrix materials are shown below:

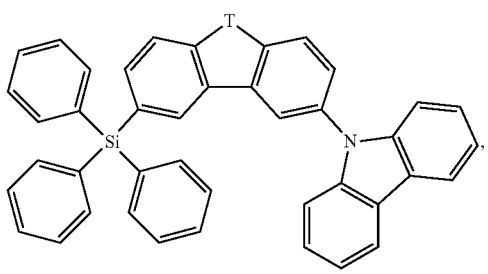

-continued
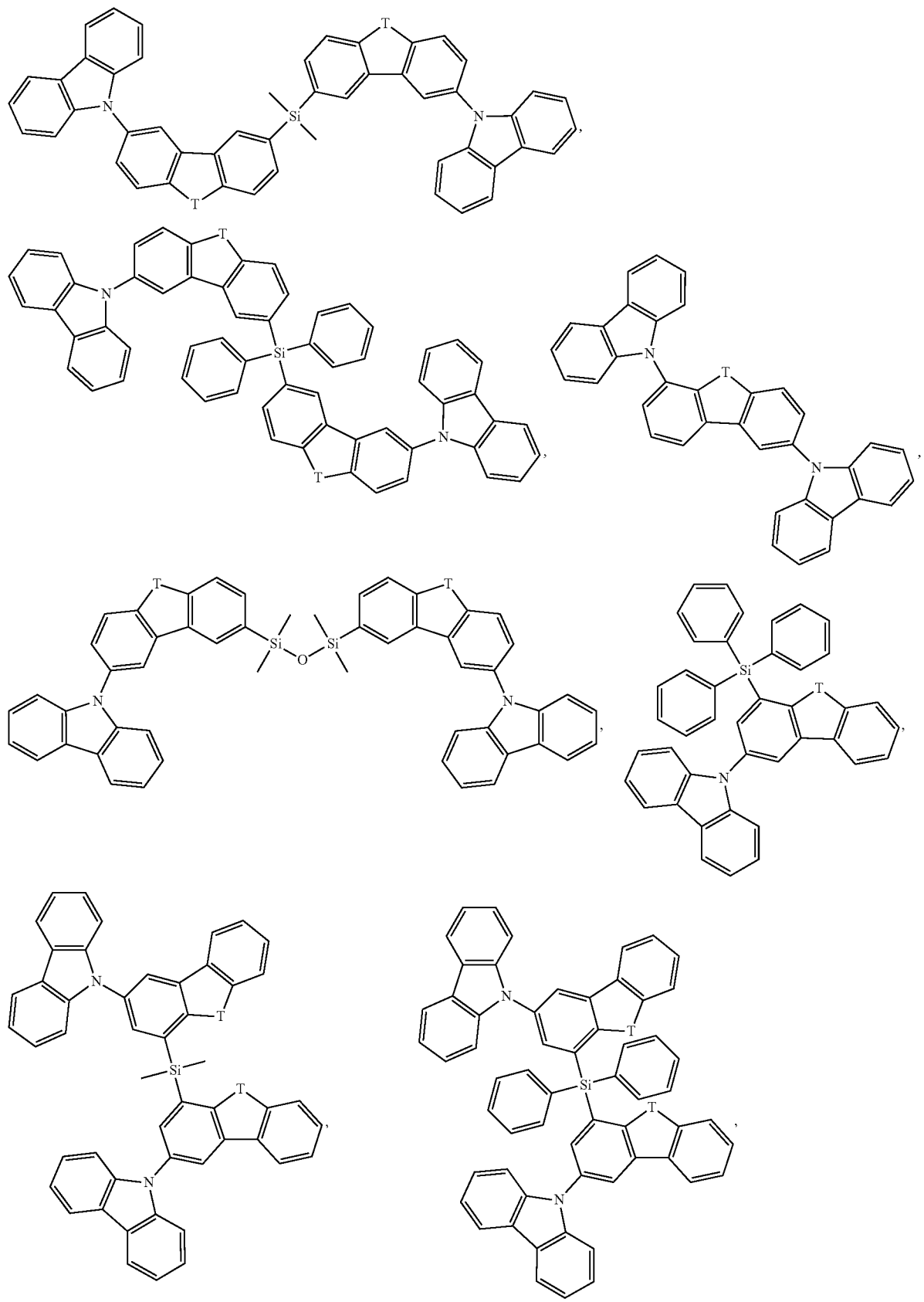

-continued
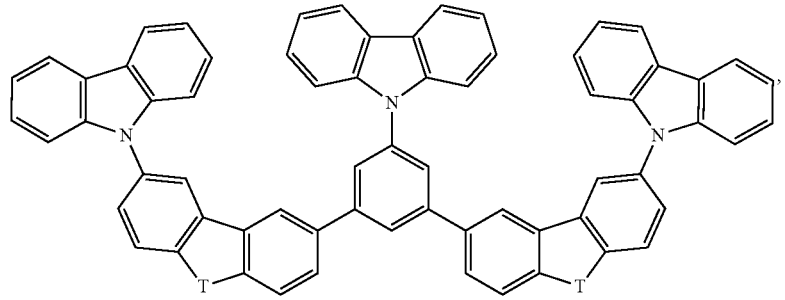
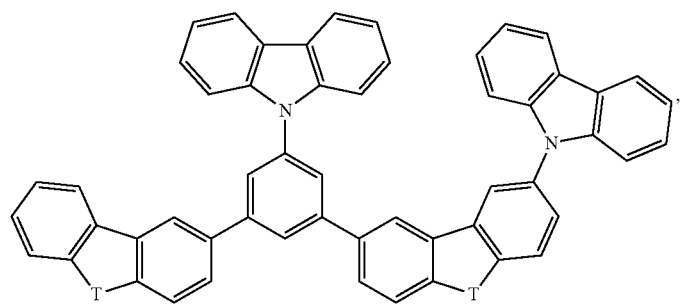
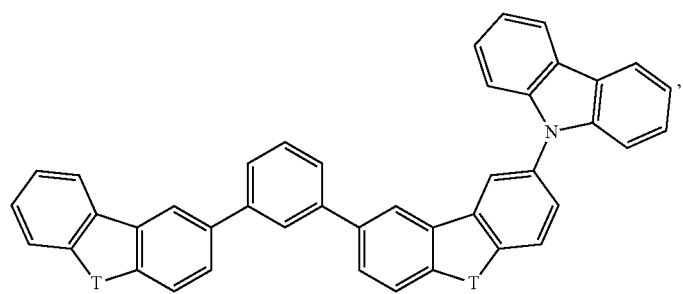
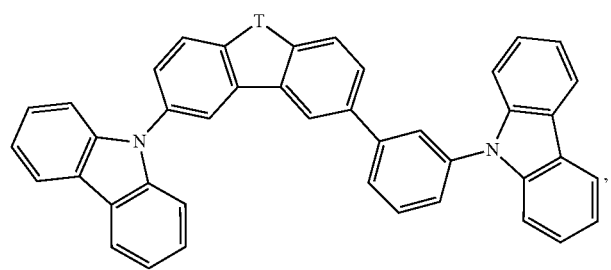
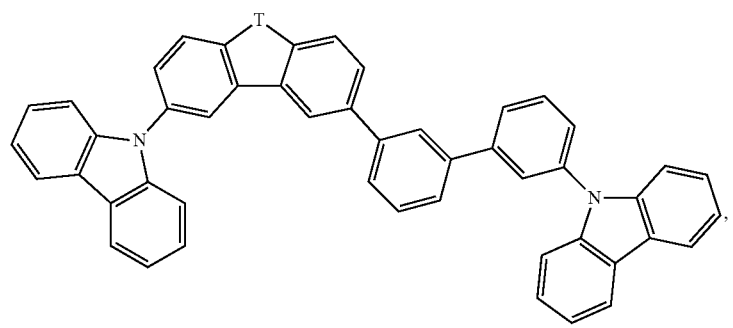

-continued
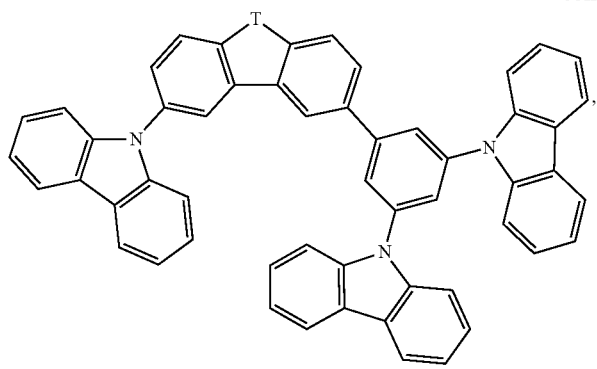
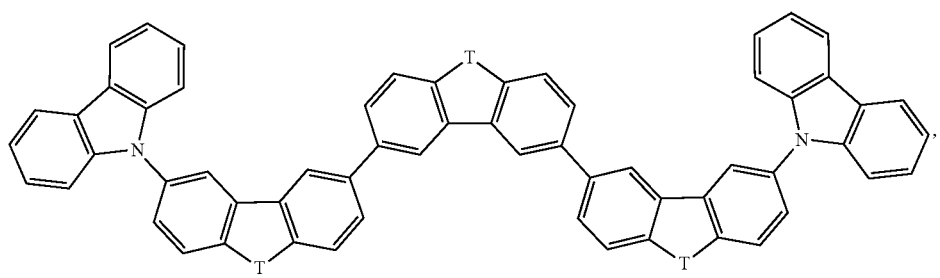
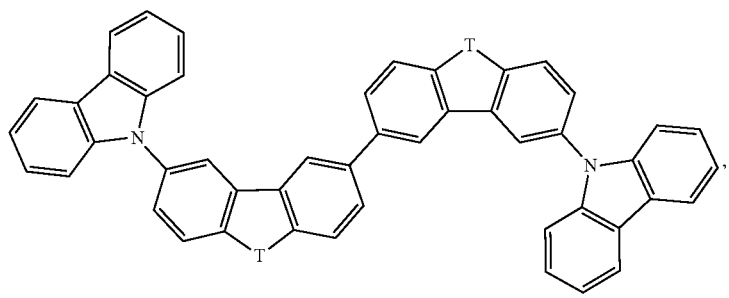
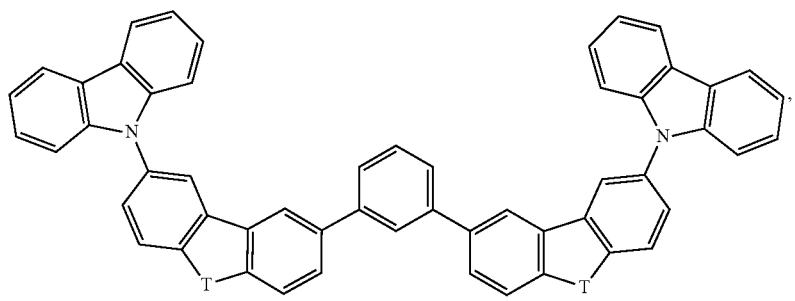
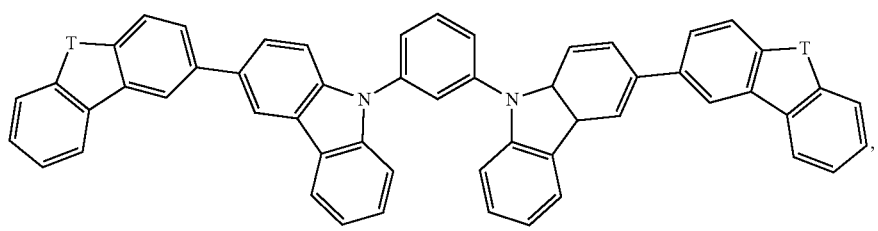

-continued
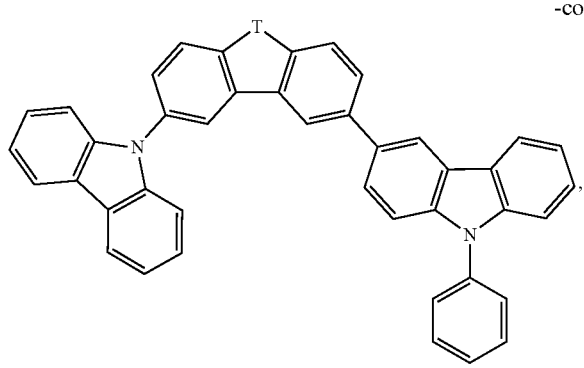
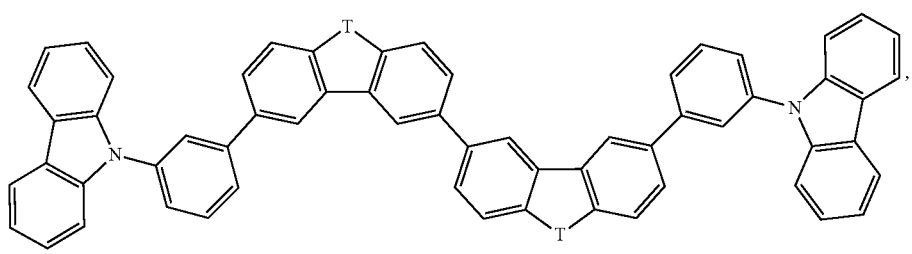
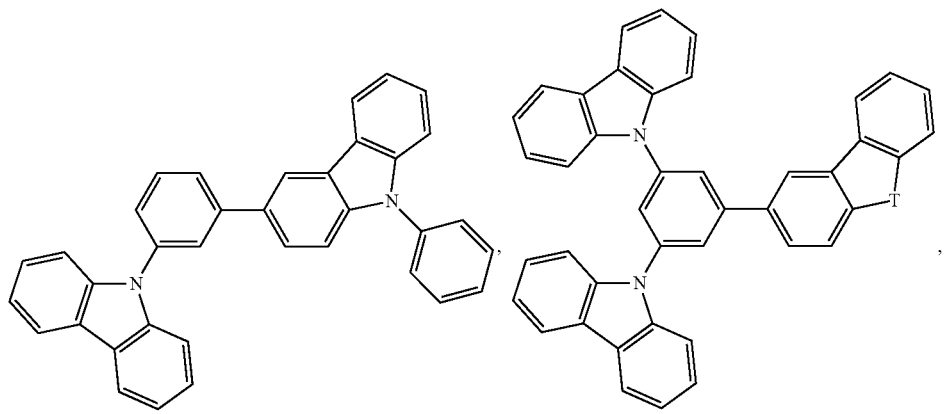
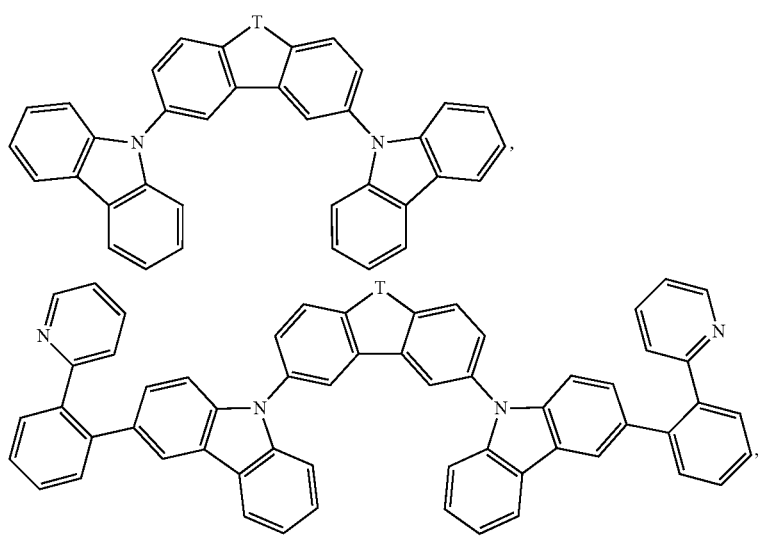

-continued
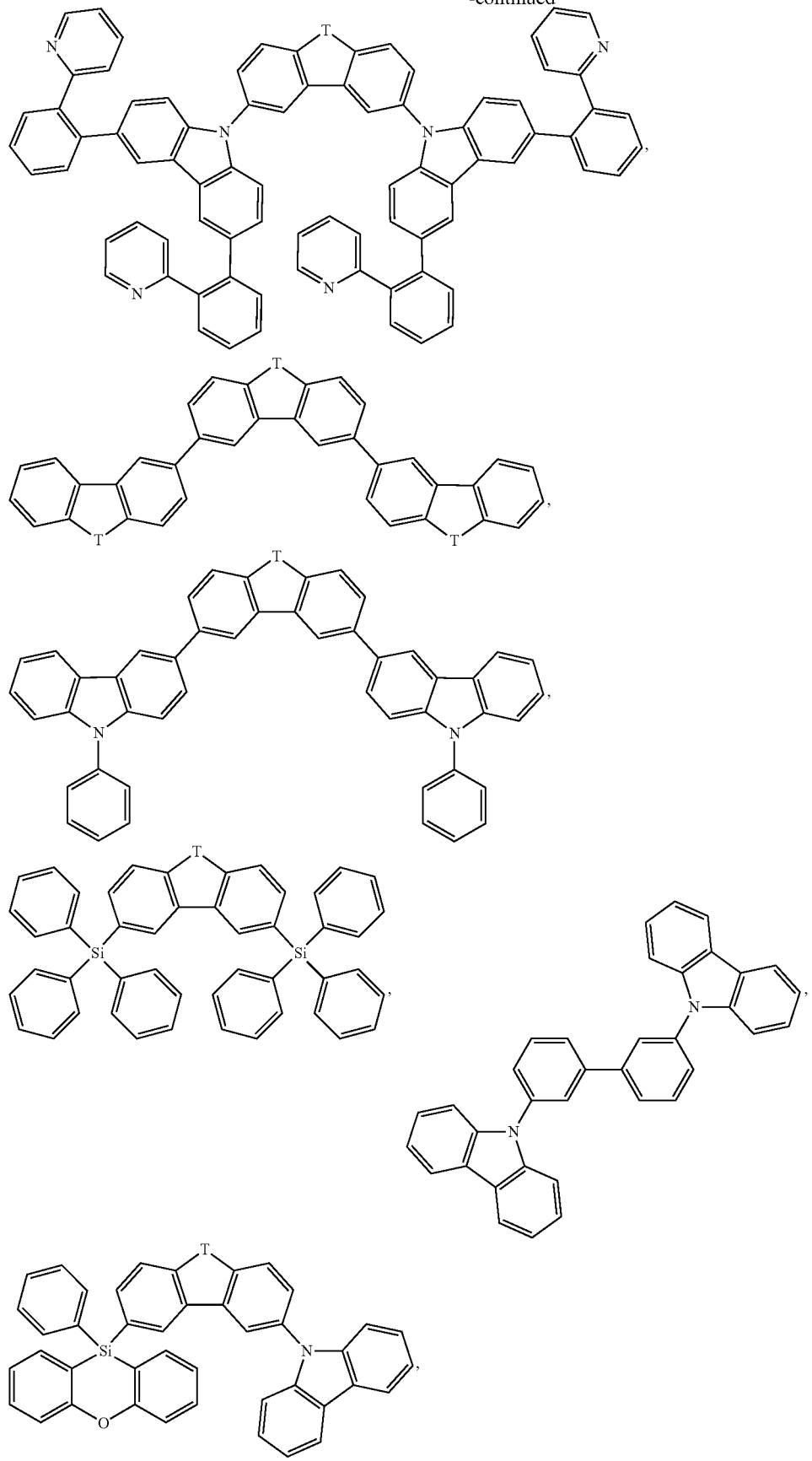

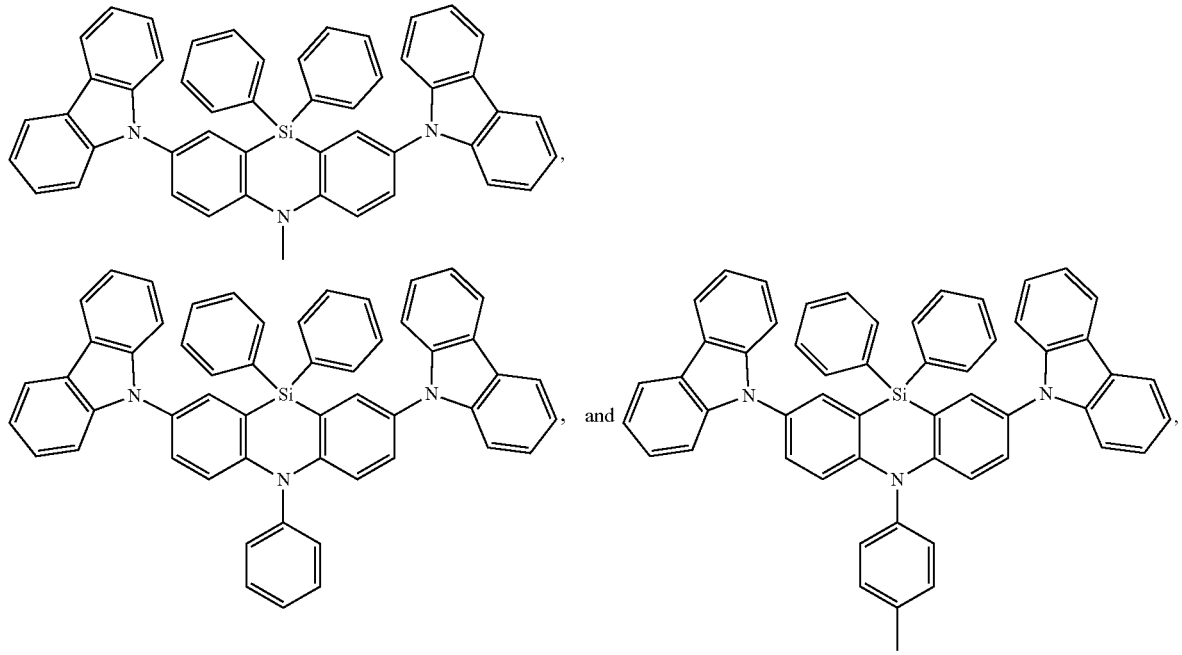

In the above-mentioned compounds T is O, or S, preferably O. If T occurs more than one time in a molecule, all groups T have the same meaning.

In a particularly preferred embodiment of the present invention compounds of the formula I, especially Group I substituted compounds of formula I, such as, for example, A-1 to A-9 and B-1 to B-9, are used in the light-emitting layer as matrix material (host) together with phosphorescent materials (triplet emitters) described, for example, in WO06/000544, WO2008/101842, and WO2009100991. Examples of phosphorescent materials are compounds A-1 to B-234, B-1 to B-234, C-1 to C-44 and D-1 to D-234, which are described in WO2008/101842. Preferred examples are described in WO2009100991 example 48-53, 54-78.

In a further embodiment, the compounds of the formula X are used as hole/exciton blocker material, preferably together with a triplet emitter describe above. The compounds of the formula X may be used as matrix materials or both as matrix materials and as hole/exciton blocker materials together with a triplet emitter described above. Suitable metal complexes for use together with the compounds of the formula X as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

Hole blocker materials typically used in OLEDs are compounds of formula X, 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-conducting material. Further suitable hole blockers and/or electron transport materials are 2,2',2''-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris-(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]-phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in WO2009003919 (PCT/EP2008/058207) and WO2009003898 (PCT/EP2008/058106) and disilyl compounds as disclosed in WO2008/034758, as a blocking layer for holes/excitons (4) or as matrix materials in the light-emitting layer (3).

In a preferred embodiment, the present invention relates to an inventive OLED comprising the layers (1) anode, (2) hole transport layer, (3) light-emitting layer, (4) blocking layer for holes/excitons, (5) electron transport layer and (6) cathode, and if appropriate further layers.

Suitable electron transport materials for the layer (5) of the inventive OLEDs comprise metals chelated to oxinoid compounds, such as 2,2',2''-(1,3,5-phenylene)tris[1-phenyl-1H-benzimidazole] (TPBI), tris(8-quinolinolato)aluminum ($Alq_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4- oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)aluminum (BAlq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HNBphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, BCP doped with $CsCO_3$ is used as the electron transport material. In principle, it is possible that the electron transport (conductor) layer comprises at least one compound of the formula (I) as electron transport material.

In addition—in one embodiment—it is possible to use Group II and III substituted compounds of formula I, such as, for example, C-1 to C-6, D-1 to D-6, E-1 to E-20 and F-1 to F-20 as electron transport materials.

Among the materials mentioned above as hole transport materials and electron transport materials, some may fulfil several functions. For example, some of the electron-transporting materials are simultaneously hole-blocking materials when they have a low-lying HOMO. These can be used, for example, in the blocking layer for holes/excitons (4).

The charge transport layers can also be electronically doped in order to improve the trans-port properties of the materials used, in order firstly to make the layer thicknesses more generous (avoidance of pinholes/short circuits) and in order secondly to minimize the opersting voltage of the device. For example, the hole transport materials can be doped with electron acceptors; for example, phthalocyanines or arylamines such as TPD or TDTA can be doped with tetrafluorotetracyanquinodimethane (F4-TCNQ) or with $MoO_3$ or $WO_3$. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole trans-port layer may, in addition to a carbene complex, e.g. Ir(dpbic)$_3$, be doped with $MoO_3$, $ReO_3$, or $WO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, lithium-comprising organometallic compounds or potassium fluoride (KF) can be applied between the organic layer and the cathode in order to reduce the operating voltage.

The OLED according to the present invention may additionally comprise further layers which are known to those skilled in the art. For example, a layer which facilitates the trans-port of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the trans-port of negative charge and/or to match the band gaps between the layers to one another. Alternatively, this layer may serve as a protective layer.

In a preferred embodiment, the inventive OLED, in addition to layers (1) to (6), comprises at least one of the following layers mentioned below:
a hole injection layer between the anode (1) and the hole-transport layer (2);
a blocking layer for electrons between the hole-transport layer (2) and the light-emitting layer (3);
an electron injection layer between the electron-transport layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino)phenyl]benzidine (NPNPB), N,N'-di(naphthalen-2-yl)-N,N'-diphenylbenzene-1,4-diamine (α-NPP). In principle, it is possible that the hole injection layer comprises at least one compound of the formula X as hole injection material. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl] (Plexcore® OC Conducting Inks commercially available from Plextronics), and copolymers such as poly(3,4-ethylenedioxythiophene)/poly(4-styrenesulfonate) also called PEDOT/PSS.

As a material for the electron injection layer, KF, or

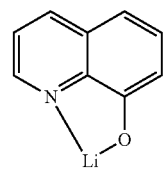

(8-hydroxyquinolinolato-lithium (Liq)), for example, can be selected. KF is more preferred than Liq.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semitransports, typically ITO, or IZO, or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer have greater thicknesses than the layer thicknesses specified when they are electrically doped.

Use of the electron transport layer of the present application makes it possible to obtain OLEDs with high efficiency and with low operating voltage. Frequently, the OLEDs obtained by the use of the electron transport layer of the present application additionally have high lifetimes. The efficiency of the OLEDs can additionally be improved by optimizing the other layers of the OLEDs. Shaped substrates and novel hole-transport materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; items of clothing; furniture; wallpaper.

In addition, the compounds of the present application can be used in OLEDs with inverse structure. The structure of inverse OLEDs and the materials typically used therein are known to those skilled in the art.

In addition, the present invention relates to an apparatus selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; items of clothing; furniture; wallpaper, comprising the inventive organic electronic device, or the inventive the hole transport, or electron transport layer.

The following examples are included for illustrative purposes only and do not limit the scope of the claims. Unless otherwise stated, all parts and percentages are by weight.

EXAMPLES

Example 1

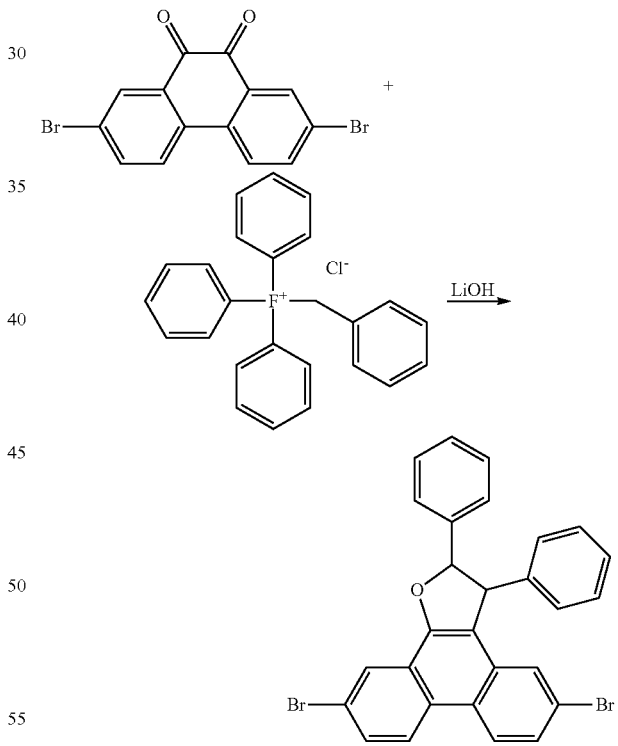

a) 6.88 g (164 mmol) lithium hydroxide monohydrate in 50 ml water are added to 20 g 54.6 mmol) 2,7-dibromophenanthrene-9,10-dione and 43.6 g (112 mmol) benzyl(triphenyl) phosphonium chloride in 200 ml methylen chloride. The reaction mixture is stirred at 25° C. for 4 h. The organic phase is separated and dried with magnesium sulphate. The solvent is distilled off and the product is decocted in ethanol (yield: 20 g (69%)).

$^1$H NMR (300 MHz, CDCl$_3$, δ): 8.53 (d, J=8.9 Hz, 1H), 8.42-8.46 (m, 2H), 7.83 (dd, J=8.9 Hz, J=2.1 Hz, 1H), 7.53

(dd, J=2.1 Hz, J=8.9 Hz, 1H), 7.25-7.45 (m, 11H), 5.84 (d, J=5.8 Hz, 1H), 4.95 (d, J=5.8 Hz, 1H).

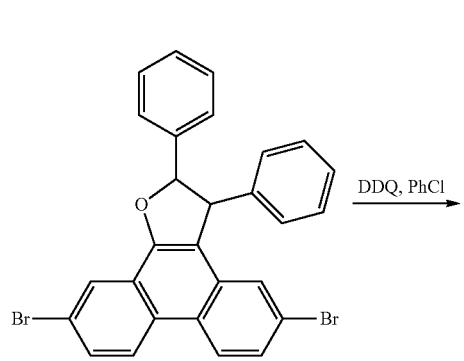

b) 2.50 g (11.0 mmol) 2,3-dichloro-5,6-dicyanobenzoquinone (DDQ) are added to 5.6 g (10.0 mmol) of 5,10-dibromo-2,3-diphenyl-2,3-dihydrophenanthro[9,10-b]furan in 25 ml chlorobenzene. The reaction mixture is refluxed for 2 h under nitrogen, dichloromethane is added and the reaction mixture is washed with a sodium hydrogen carbonate solution. The organic phase is dried with magnesium sulphate. The solvent is distilled off and the product is decocted in dibutylether (yield: 4.80 g (91%)).

$^1$H NMR (300 MHz, CDCl$_3$, δ): 8.61 (d, J=2 Hz, 1H), 8.45-8.49 (m, 2H), 7.73 (dd, J=8.9 Hz, J=2.1 Hz, 1H), 7.54-7.64 (m, 8H), 7.27-7.37 (m, 4H).

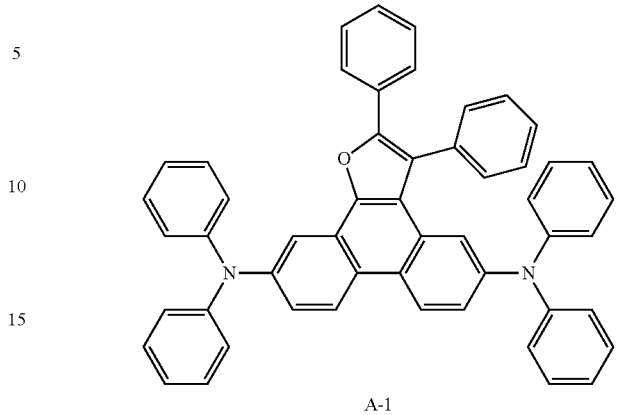

A-1 c) 2.01 g g (20.9 mmol) sodium tert-butoxide are added to 4.80 g (9.08 mmol) of the product of example 1b in 100 ml toluene. 3.38 g (20.0 mmol) N-phenylaniline are added. The reaction mixture is degassed with argon. 102 mg (0.45 mmol) palladium(II) acetate are added. The reaction mixture is degassed with argon. 184 mg (91 mmol) tri-tert-butylphosphine are added. The reaction mixture is degassed with argon. The reaction mixture is stirred for 18 h at 90° C. under argon. A 1% sodium cyanide solution is added and the mixture is extracted with dichloromethane. The organic phase is dried with magnesium sulphate. The solvent is distilled off. Column chromatography on silica gel with toluene cyclohexane 1/4 results in the product (yield: 3.18 g (50%))

$^1$H NMR (300 MHz, THF-d$_8$, δ): 8.58 (d, J=9.1 Hz, 1H), 8.54 (d, J=9.9 Hz, 1H), 8.11 (d, J=2.4 Hz, 1H), 6.95-7.45 (m, 33H).

Example 2

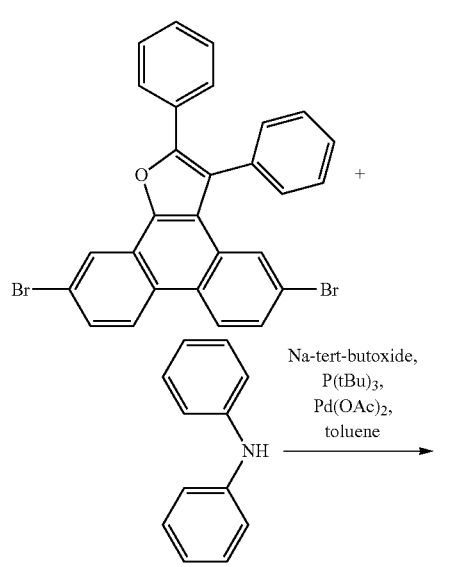

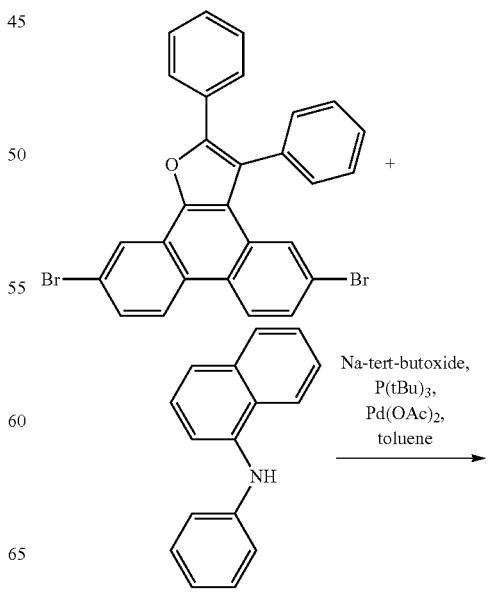

-continued

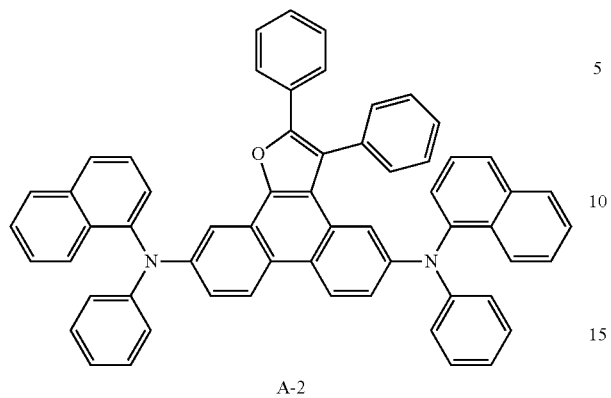

A-2

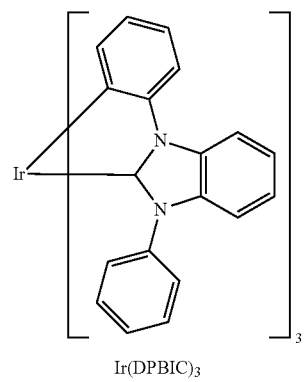

Ir(DPBIC)₃

Example 1c) is repeated, except that

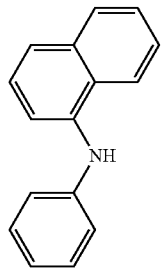 [SMILES: c1ccc(Nc2cccc3ccccc23)cc1]

is used instead of N-phenylaniline. Compound A-2 is obtained in a yield of 54%.

¹H NMR (300 MHz, Benzene-d₆, δ): 8.60 (d, J=2.4 Hz, 1H), 8.41-8.45 (m, 1H), 8.34-8.27 (m, 2H), 8.12 (d, J=8.4 Hz, 1H), 6.86-7.79 (m, 35H).

Application Example 1

The ITO substrate used as the anode is first cleaned with commercial detergents for LCD production (Deconex® 20NS, and 250RGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Then Plexcore® OC AJ20-1000 (commercially available from Plextronics Inc.) is spin-coated and dried to form a hole injection layer (~40 nm).

Thereafter, the organic materials specified below are applied by vapor deposition to the clean substrate at a rate of approx. 0.5-5 nm/min at about $10^{-7}$-$10^{-9}$ mbar. As a hole trans-port and exciton blocker, Ir(dpbic)₃ (for preparation, see Ir complex (7) in the application WO 2005/019373) is applied to the substrate with a thickness of 45 nm, wherein the first 35 nm are doped with $MoO_x$ (~10%) to improve the conductivity.

Subsequently, a mixture of 10% by weight of compound

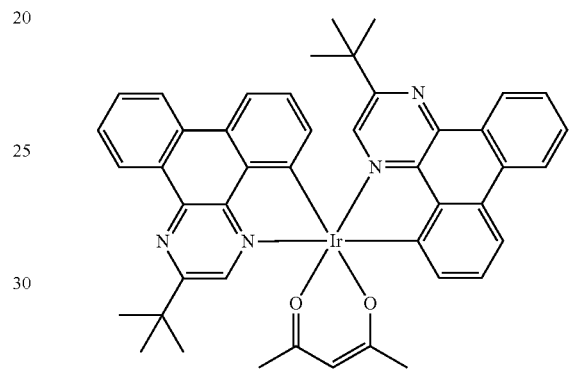

and 90% by weight of compound A-1 (matrix material) is applied by vapor deposition in a thickness of 20 nm.

Subsequently, the material bis(2-methyl-8-quinolinolato)(4-phenylphenolato)aluminum(III) (BAlq) is applied by vapor deposition with a thickness of 10 nm as exciton and hole blocker.

Next, a mixture of 93% by weight of

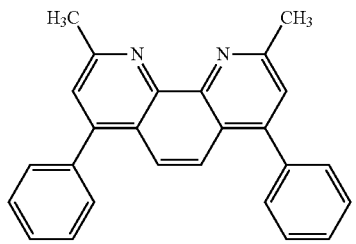 [SMILES: Cc1cc(-c2ccccc2)c2ccc3c(-c4ccccc4)cc(C)nc3c2n1]

(BCP) and 7% by weight of $Cs_2CO_3$ is applied as electron transport layer by vapor deposition in a thickness of 50 nm and finally a 100 nm-thick Al electrode is applied by vapor deposition.

All prefabricated parts are sealed with a glass lid in an inert nitrogen atmosphere.

Comparative Application Example 1

Production and construction of an OLED as in the application example 1, except α-NPD is used host instead of compound A-1.

To characterize the OLED, electroluminescence spectra are recorded at various currents and voltages. In addition, the current-voltage characteristic is measured in combination with the light output emitted. The light output can be converted to photometric parameters by calibration with a photometer. To determine the lifetime, the OLED is operated at a constant current density and the decrease in the light output is recorded. The lifetime is defined as that time which lapses until the luminance decreases to half of the initial luminance.

|  | Host | EQE[1] @ 1000 nits |
| --- | --- | --- |
| Application Example 1 | Compound A-1 | 12.4% |
| Comp. Appl. Ex. 1 | α-NPD | 11.6% |

[1]External quantum efficiency (EQE) is # of generated photons escaped from a substance or a device/# of electrons flowing through it.

The device of application example 1, where compound A-1 is used as host, shows a better external quantum efficiency as the device of comparative application example 1, where α-NPD is used as host.

Application Example 2

After the hole injection layer the organic materials specified below are applied by vapor deposition to the clean substrate at a rate of approx. 0.5-5 nm/min at about $10^{-7}$-$10^{-9}$ mbar. As a hole transport and exciton blocker α-NPD is applied to the substrate with a thickness of 20 nm, wherein the first 10 nm are doped with $MoO_x$ (~10%) to improve the conductivity.

Subsequently, a mixture of 10% by weight of compound

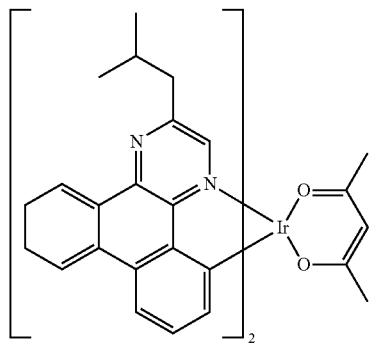

and 90% by weight of compound A-2 (matrix material) is applied by vapor deposition in a thickness of 20 nm.

Subsequently, the material BAlq is applied by vapor deposition with a thickness of 10 nm as exciton and hole blocker. Next, a mixture of 93% by weight of BCP and 7% by weight of $Cs_2CO_3$ is applied as electron transport layer by vapor deposition in a thickness of 50 nm and finally a 100 nm-thick Al electrode is applied by vapor deposition.

Comparative Application Example 2

Production and construction of an OLED as in the application example 2, except 4,4'-bis[N-(1-naphthyl)-N-phenylamino]biphenyl (α-NPD) is used host instead of compound A-2.

|  | HTL[1] | Host | Lifetime [h] @ 6000 nits |
| --- | --- | --- | --- |
| Application Example 2 | α-NPD | Compound A-2 | 893 h |
| Comp. Appl. Ex. 2 | α-NPD | α-NPD | 607 h |

[1]HTL = Hole Transport Layer.

The device of application example 2, where compound A-1 is used as host, shows a better life time than the device of comparative application example 2, where α-NPD is used as host.

Application Example 3

After the hole injection layer the organic materials specified below are applied by vapor deposition to the clean substrate at a rate of approx. 0.5-5 nm/min at about $10^{-7}$-$10^{-9}$ mbar. As a hole transport and exciton blocker compound A-2 is applied to the substrate with a thickness of 20 nm, wherein the first 10 nm are doped with $MoO_x$ (~10%) to improve the conductivity.

Subsequently, a mixture of 10% by weight of compound

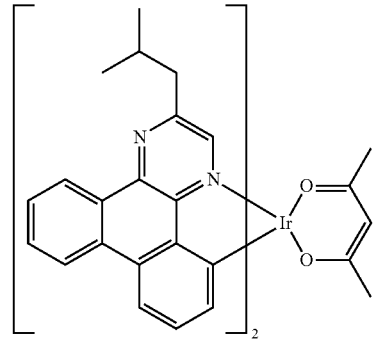

and 90% by weight of α-NPD (matrix material) is applied by vapor deposition in a thickness of 20 nm.

Subsequently, the material BAlq is applied by vapor deposition with a thickness of 10 nm as exciton and hole blocker. Next, a mixture of 93% by weight of

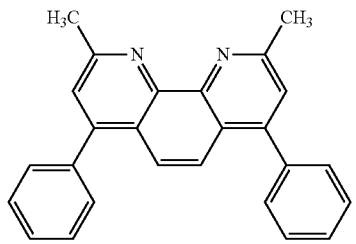 [SMILES: Cc1cc(-c2ccccc2)c2ccc3c(-c4ccccc4)cc(C)nc3c2n1]

(BCP) and 7% by weight of $Cs_2CO_3$ is applied as electron transport layer by vapor deposition in a thickness of 50 nm and finally a 100 nm-thick Al electrode is applied by vapor deposition.

|  | HTL | Host | Lifetime [h] @ 6000 nits |
| --- | --- | --- | --- |
| Application Example 3 | Cpd. A-2 | α-NPD | 1349 h |
| Comp. Appl. Ex. 2 | α-NPD | α-NPD | 607 h |

The device of application example 3, where compound A-1 is used as hole transport material (HTM), shows a better life time than the device of comparative application example 2, where α-NPD is used as HTM.

Example 3

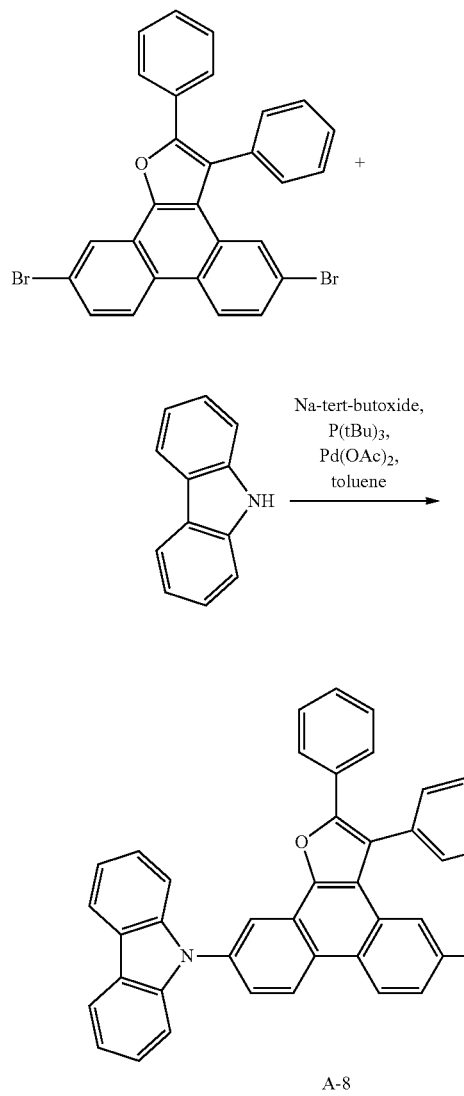

A-8

0.84 g (8.74 mmol) sodium tert-butoxide are added to 2.10 g (3.98 mmol) of the product of example 1b in 60 ml toluene. 0.70 g (8.37 mmol) carbazole are added. The reaction mixture is degassed with argon. 43 mg (0.19 mmol) palladium(II) acetate are added. 77 mg (0.38 mmol) tri-tert-butylphosphine are added. The reaction mixture is stirred for 24 h at 100° C. under argon. The reaction mixture is filtered through a plug of silica gel, and the solvent of the filtrate is distilled off. Column chromatography on silica gel with toluene cyclohexane 1/4 results in the product (compound A-8) (yield: 1.31 g (47%))

$^1$H NMR (500 MHz, THF-d$_8$, δ): 8.96 (t, J=8.1 Hz, 2H), 8.75 (s, 1H), 8.24 (d, J=7.8 Hz, 2H), 8.12 (d, J=7.7 Hz, 2H), 7.89-7.92 (m, 2H), 7.84 (d, J=8.7 Hz, 1H), 7.63 (d, J=8.1 Hz, 2H), 7.55-7.60 (m, 4H), 7.50 (t, J=7.6 Hz, 2H), 7.35-7.44 (m, 8H), 7.30 (t, J=7.2 Hz, 2H), 7.22-7.28 (m, 4H).

Example 4

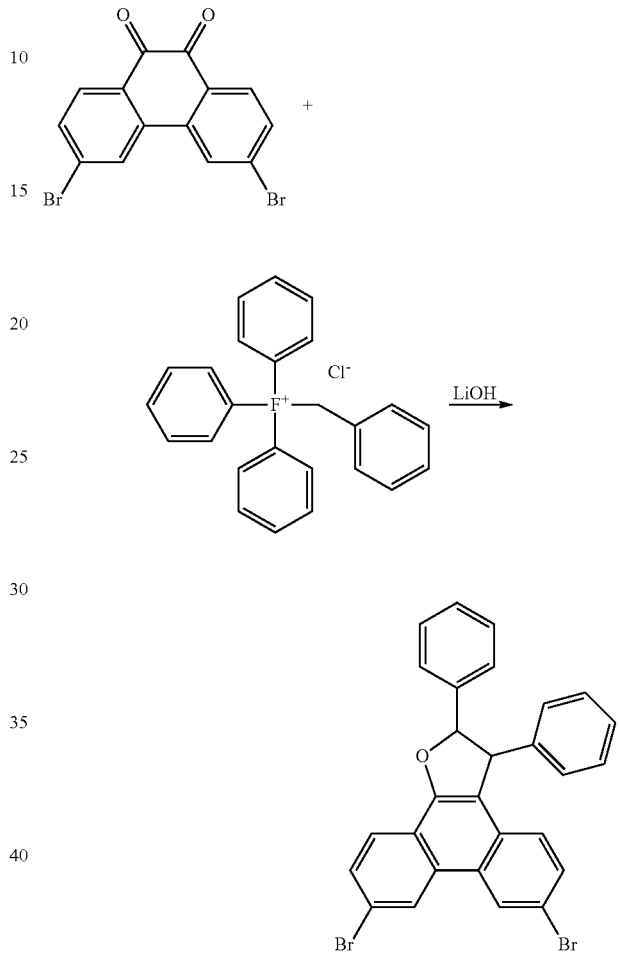

a) 1.96 g (81.9 mmol) lithium hydroxide in 25 ml water are added to 10.0 g (27.3 mmol) 3,6-dibromophenanthrene-9,10-dione (Brunner, Klemens; Dijken, Addy van; Boerner, Herbert; Bastiaansen, Jolanda J. A. M.; Kiggen, Nicole M. M.; Langeveld, Bea M. W.; J. Am. Chem. Soc. 126 (2004) 6035-6042) and 21.7 g (55.8 mmol) benzyl(triphenyl)phosphonium chloride in 230 ml methylene chloride. The reaction mixture is stirred at 25° C. for 20 h. 100 ml water are added and the organic layer is separated. The aqueous layer is extracted with methylene chloride and the combined organic phases are dried with sodium sulphate. The solvent is distilled off and the product is decocted in ethanol (yield: 10.4 g (72%)).

$^1$H NMR (400 MHz, CDCl$_3$, δ): 8.76 (d, J=1.6 Hz, 1H), 8.67 (d, J=1.7 Hz, 1H), 8.14 (d, J=8.6 Hz, 1H), 7.80 (dd, J=8.5 Hz and 1.7 Hz, 1H), 7.43 (dd, J=8.7 Hz and 1.8 Hz, 1H), 7.30-7.40 (m, 8H), 7.22-7.25 (m, 2H), 7.15 (d, J=8.6 Hz, 1H), 5.80 (d, J=6.2 Hz, 1H), 4.94 (d, J=6.2 Hz, 1H).

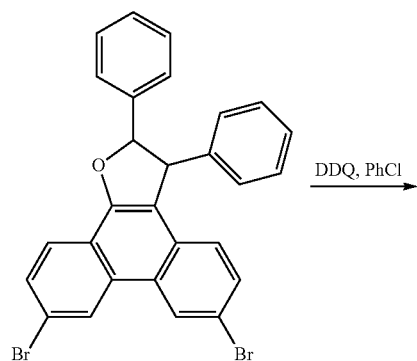

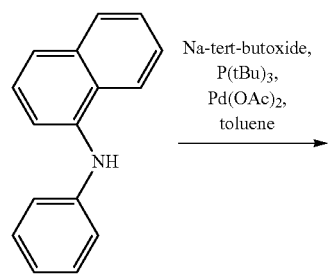

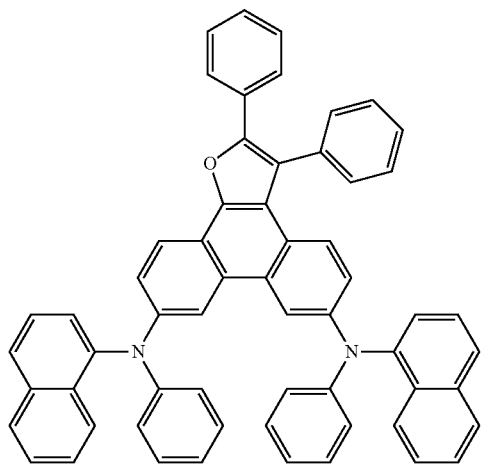

B-2 b) 4.70 g (20.7 mmol) 2,3-dichloro-5,6-dicyanobenzoquinone (DDQ) are added to 10.0 g (18.8 mmol) of 6,9-dibromo-2,3-diphenyl-2,3-dihydrophenanthro[9,10-b]furan in 50 ml chlorobenzene. The reaction mixture is refluxed for 4 h under nitrogen, dichloromethane is added and the reaction mixture is washed with a sodium hydrogen carbonate solution. The organic phase is dried with magnesium sulphate. The solvent is distilled off and the product is decocted in dibutylether. Column chromatography on silica gel with toluene cyclohexane 4/1 results in the product (yield: 5.40 g (54%)).

$^1$H NMR (400 MHz, CDCl$_3$, δ): 8.65 (d, J=10.9 Hz, 2H), 8.29 (d, J=8.6 Hz, 1H), 7.79 (d, J=8.6 Hz, 1H), 7.49-7.59 (m, 7H), 7.34-7.43 (m, 2H), 7.26-7.32 (m, 3H).

c) 0.42 g (4.35 mmol) sodium tert-butoxide are added to 1.00 g (1.89 mmol) of the product of example 4b in 15 ml toluene. 0.91 g (4.16 mmol) N-phenyl-N-naphthylamine are added. The reaction mixture is degassed with argon. 21 mg (0.09 mmol) palladium(II) acetate are added. 38 mg (0.19 mmol) tri-tert-butylphosphine are added. The reaction mixture is stirred for 18 h at 100° C. under argon. The reaction mixture is filtered through a plug of silica gel, and the solvent of the filtrate is distilled off. Column chromatography on silica gel with toluene cyclohexane 1/4 results in the product (B-2) (yield: 540 mg (35%))

$^1$H NMR (360 MHz, THF-d$_8$, δ): 8.58 (d, J=9.0 Hz, 1H), 7.84-7.94 (m, 4H), 7.73-7.82 (m, 4H), 6.88-7.57 (m, 31H).

Example 5

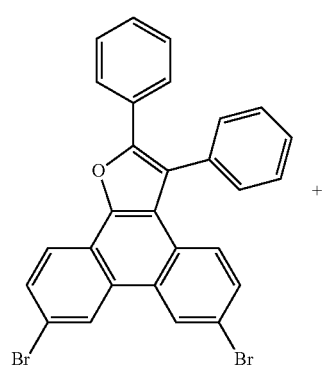 +

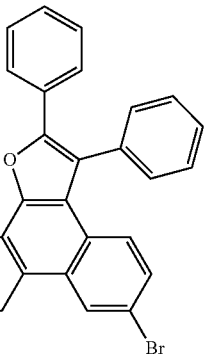 +

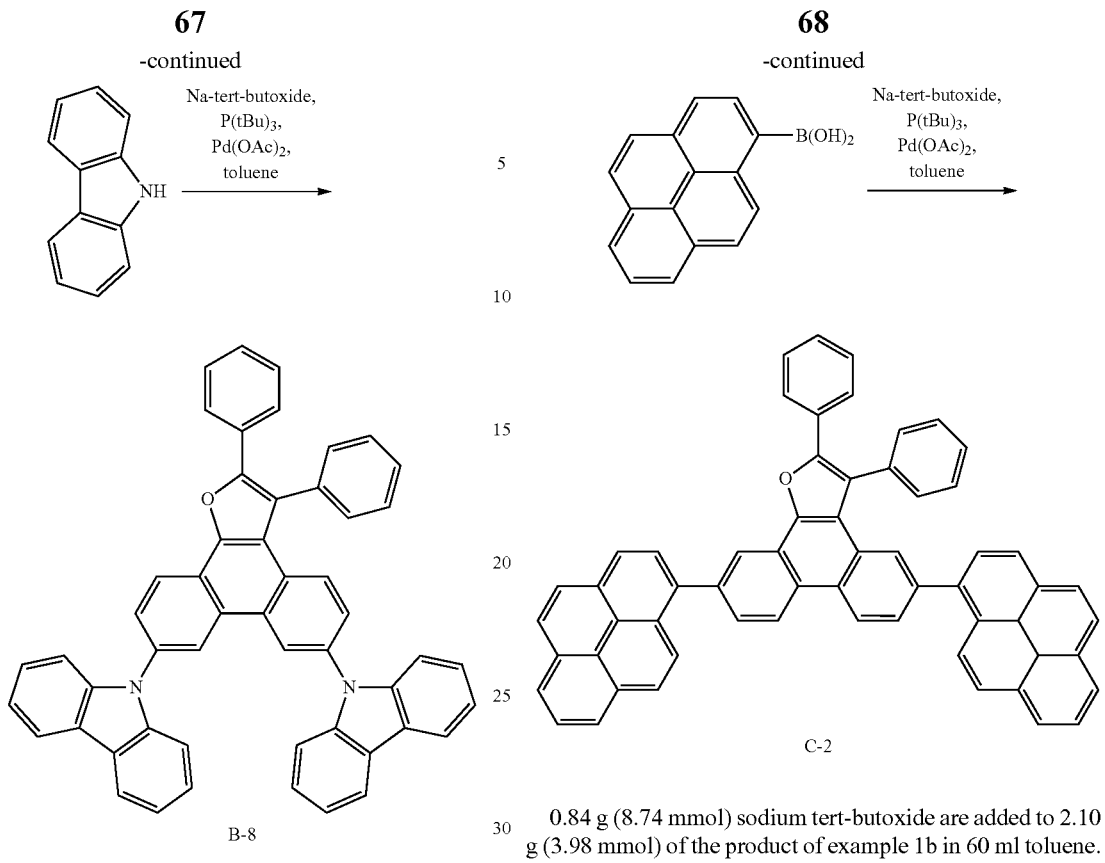

0.42 g (4.35 mmol) sodium tert-butoxide are added to 1.00 g (1.89 mmol) of the product of example 4b in 30 ml toluene. 0.70 g (4.19 mmol) carbazole are added. The reaction mixture is degassed with argon. 21 mg (0.09 mmol) palladium(II) acetate are added. 38 mg (0.19 mmol) tri-tert-butylphosphine are added. The reaction mixture is stirred for 24 h at 100° C. under argon. The reaction mixture is filtered through a plug of silica gel, and the solvent of the filtrate is distilled off. Column chromatography on silica gel with toluene cyclohexane 1/4 results in the product (B-8; yield: 720 mg (54%))

$^1$H NMR (400 MHz, THF-d$_8$, δ): 9.13 (d, J=9.8 Hz, 2H), 8.65 (d, J=8.6 Hz, 1H), 8.07-8.15 (m, 4H), 8.03 (d, J=8.5 Hz, 1H), 7.91 (d, J=8.7 Hz, 1H), 7.60-7.74 (m, 8H), 7.49 (d, J=8.2 Hz, 2H), 7.14-7.42 (m, 13H).

0.84 g (8.74 mmol) sodium tert-butoxide are added to 2.10 g (3.98 mmol) of the product of example 1b in 60 ml toluene. 2.10 g (8.53 mmol) pyrene-1-boronic acid are added. The reaction mixture is degassed with argon. 43 mg (0.19 mmol) palladium(II) acetate are added. 77 mg (0.38 mmol) tri-tert-butylphosphine are added. The reaction mixture is stirred for 24 h at 100° C. under argon. Methylene chloride is added to the reaction mixture, and the undissolved residue is filtered off and discarded. The solvent of the filtrate is distilled off. Column chromatography on silica gel with n-hexane ethyl acetate 9/1 results in the product (yield: 290 mg (10%)). MS (MALDI (pos): m/z (%)): 770 (M$^+$, 100%).

Example 7

Example 6

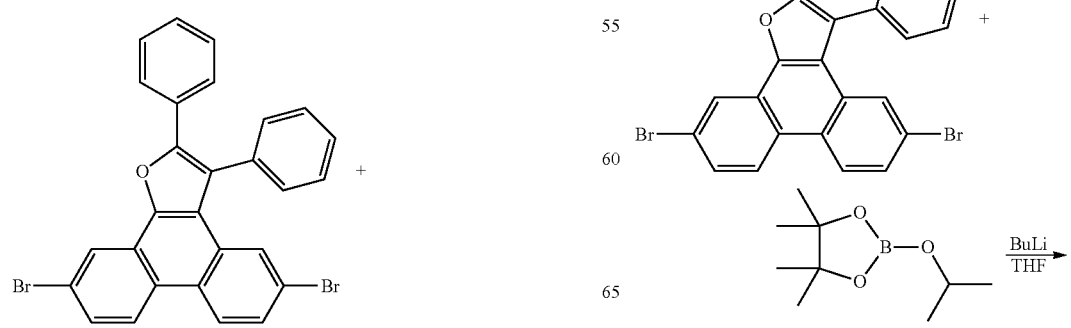

-continued

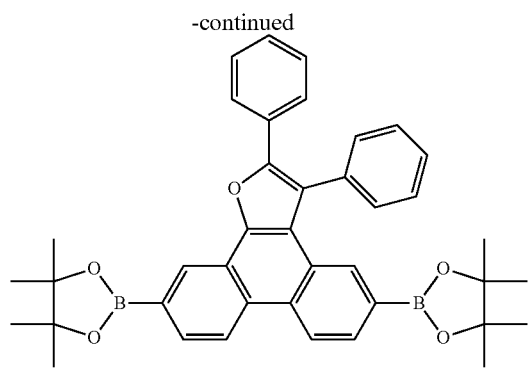

a) 7.2 ml (18.0 mmol) of a 2.5 M n-butyl lithium solution in hexane are added to 3.95 g (7.48 mmol) of the product of example 1b) in water free tetrahydrofuran (THF) under argon at −78° C. The reaction mixture is stirred for 30 minutes at −78° C. 3.90 g (20.9 mmol) 2-isopropoxy-4,4',5,5'-tetramethyl-1,3,2-dioxaborolan are added. The reaction mixture is stirred for 30 minutes and is then warmed up to 25° C., poured into water and the water phase is extracted with diethyl ether and dichloromethane. The organic phase is dried with magnesium sulfate and the solvent is distilled off. The product is used without purification for the next reaction step.

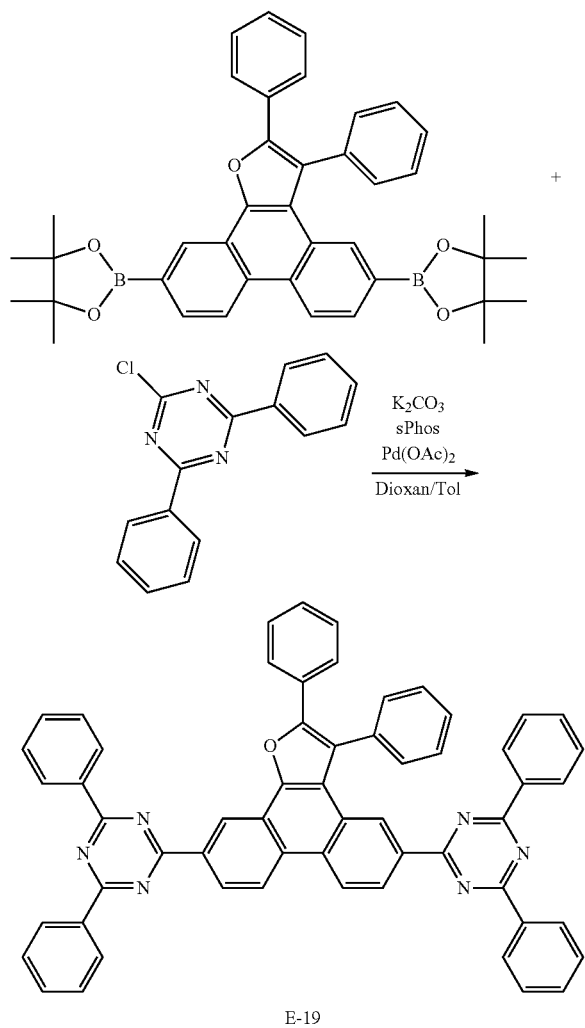

b) 10 ml of a 2M solution of potassium carbonate in water are added to 1.80 g (2.89 mmol) of the product of example 7a) and 1.70 g (6.36 mmol) 2-chlor-4,6-diphenyl-1,3,5-triazine in a mixture of 10 ml dioxane and 50 ml toluene. Then the reaction mixture is degassed with argon. 143 mg (0.35 mmol) 2-dicyclohexylphosphino-2',6'-dimethoxybiphenyl (sPhos) and 6.5 mg (0.029 mmol) palladium(II) acetate are added and the reaction mixture is stirred for 24 h at 120° C. under argon. 40 ml of a 1% solution of sodium cyanide water are added and the reaction mixture is stirred at 100° C. for 1 h. The solvent is destilled off and the product is filtered off. The product is washed with water and ethanol. Column chromatography on silica gel with toluene, toluene/ethylacetate 10/1, toluene/ethylacetate 1/1 and toluene/ethanol 10/1 results in the product (E-19; yield: 41 mg (2%)). MS (APCI (pos): m/z (%): 833 ($M^{+1}$, 100%).

The invention claimed is:

1. A compound of formula (I):

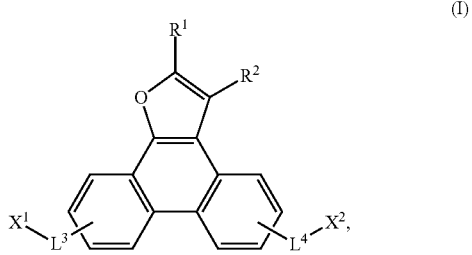

wherein $R^1$ and $R^2$ are a group of formula

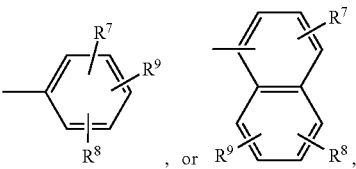

$R^7$, $R^8$ and $R^9$ are independently of each other H, $C_1$-$C_{18}$alkyl, $C_1$-$C_{18}$alkoxy, or $C_1$-$C_{18}$alkyl which is interrupted by O;

wherein -$L^3$-$X^1$ and -$L^4$-$X^2$ are independently of each other a group of formula -$NA^1A^{1'}$, or a group

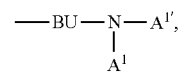

$A^1$ and $A^{1'}$ are independently of each other

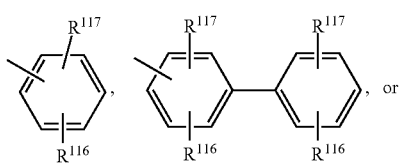

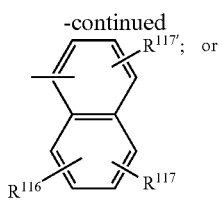

$A^1$ and $A^{1'}$ together with a nitrogen atom to which they are bonded form a heteroaromatic ring, or form a structure

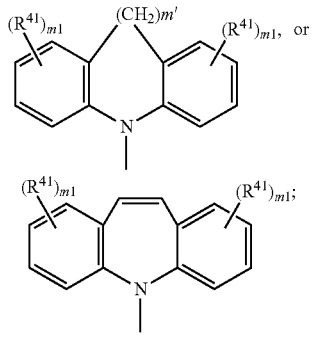

m' is 0, 1, or 2; m1 can be same or different at each occurrence and is 0, 1, 2, 3, or 4;

$R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{77}$, —C(=O)O$R^{78}$, or —C(=O)N$R^{75}R^{76}$, $R^{75}$, $R^{76}$ and $R^{78}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{77}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, BU is

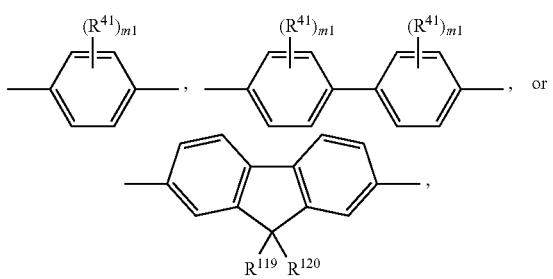

$R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =C$R^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring selected from the group consisting of cyclohexyl and cyclopentyl, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{28}$, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —SO$_2$—, —O—, —N$R^{65}$—, —Si$R^{70}R^{71}$—, —POR$^{72}$—, —C$R^{63}$=C$R^{64}$—, or —C≡C—, and E is —O$R^{69}$, —S$R^{69}$, —N$R^{65}R^{66}$, —COR$^{68}$, —COOR$^{67}$, —CONR$^{65}R^{66}$, —CN, or halogen, G is E, or $C_1$-$C_{18}$alkyl, $R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl;

$R^{41}$ can be the same or different at each occurrence and is Cl, F, CN, N$R^{45}R^{45'}$, a $C_1$-$C_{25}$alkyl group, a $C_4$-$C_{18}$cycloalkyl group, a $C_1$-$C_{25}$alkoxy group, wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$;

$R^{45}$ and $R^{45'}$ are independently of each other a $C_1$-$C_{25}$alkyl group, a $C_4$-$C_{18}$cycloalkyl group, wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$;

-$L^3$-$X^1$ and -$L^4$-$X^2$ are independently of each other a group of formula

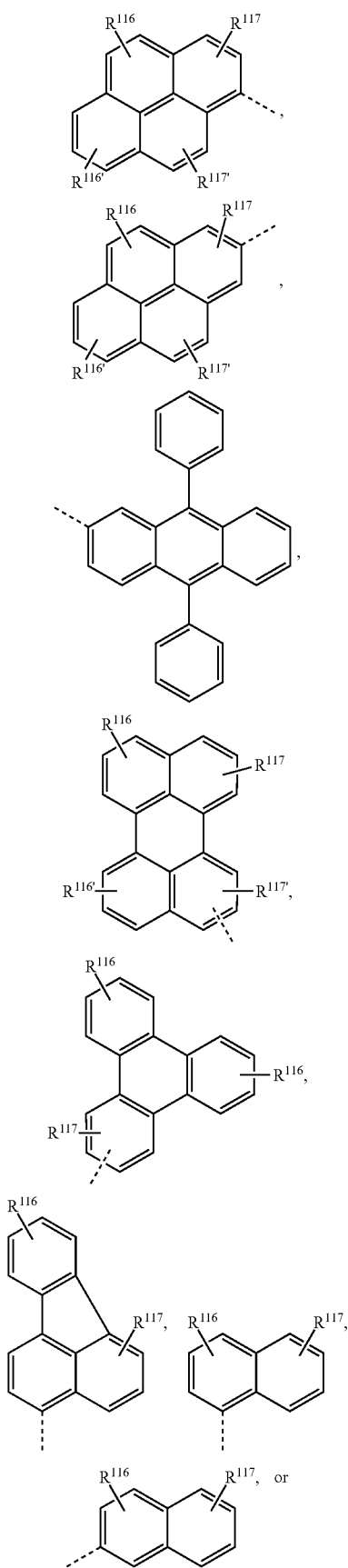
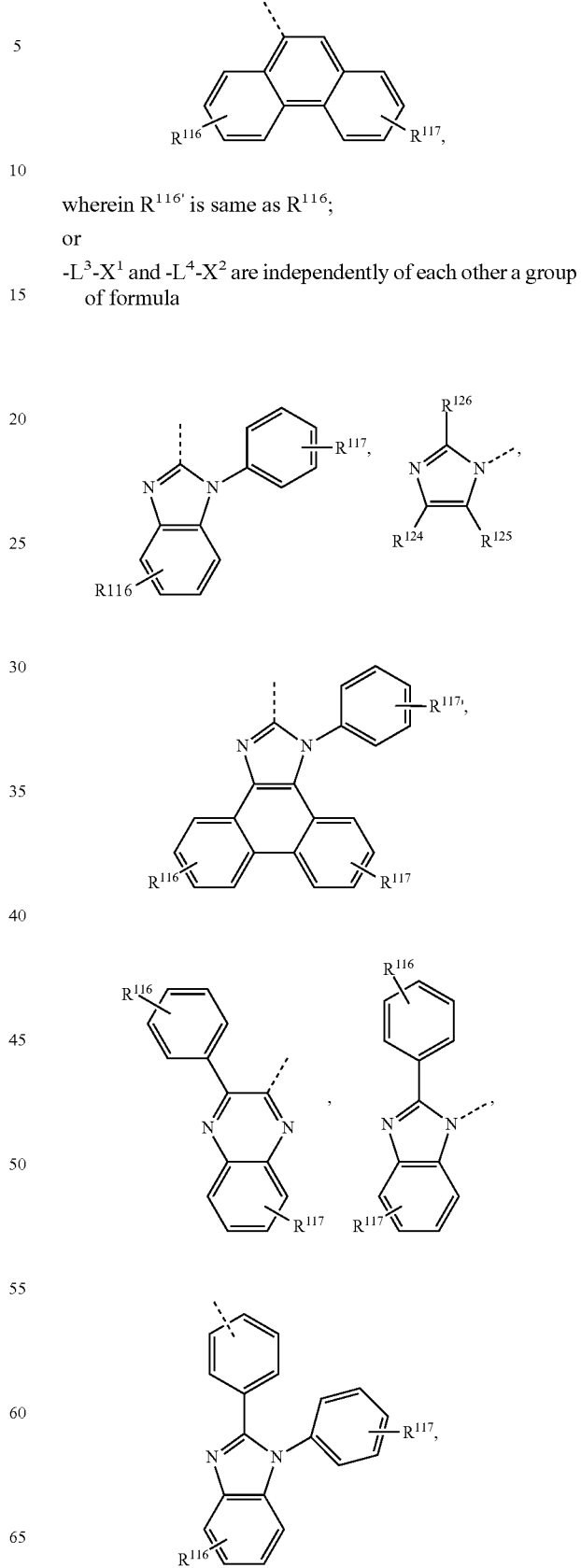
wherein $R^{116'}$ is same as $R^{116}$; or
-$L^3$-$X^1$ and -$L^4$-$X^2$ are independently of each other a group of formula

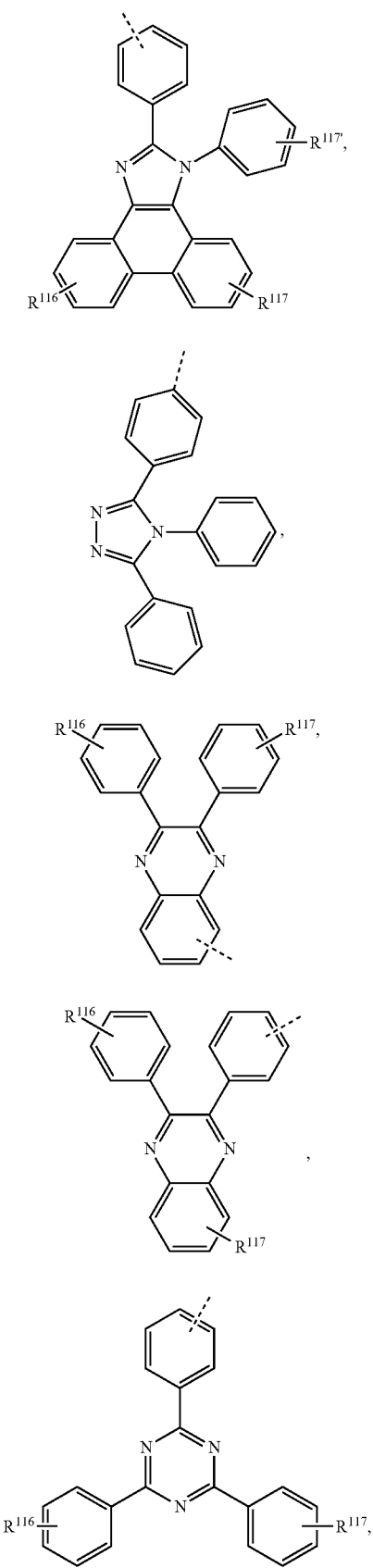

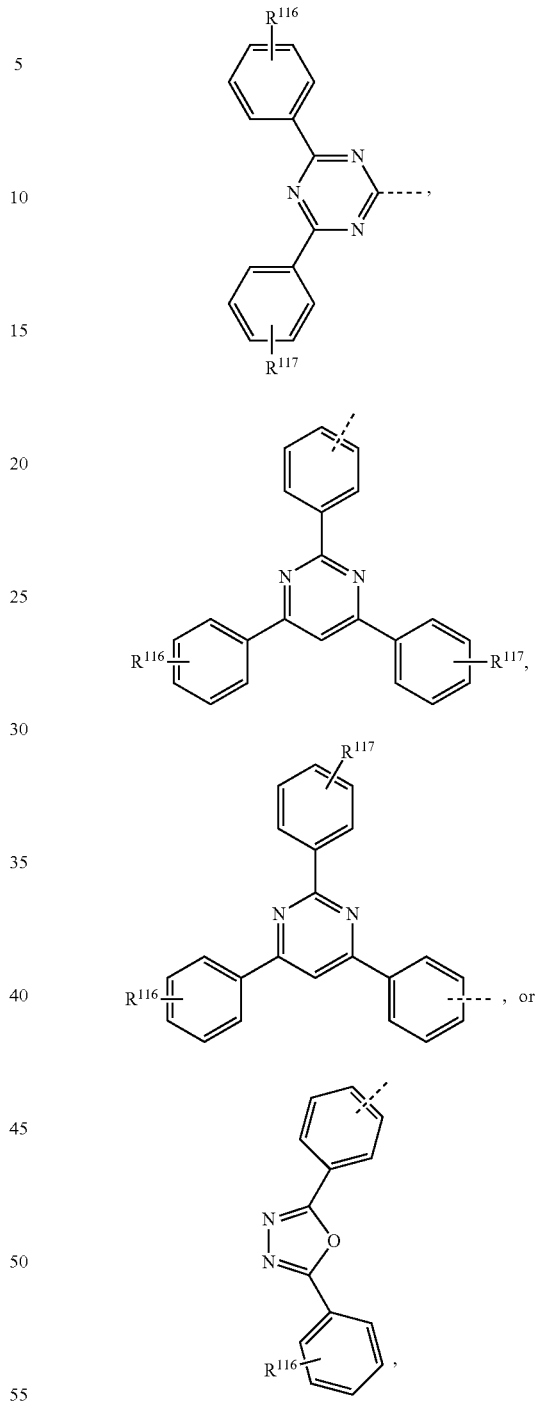

$R^{124}$, $R^{125}$ and $R^{126}$ are independently of each other H, $C_1$-$C_{18}$alkyl, $C_1$-$C_{18}$alkyl which is substituted by E and/or interrupted by D, $C_1$-$C_{18}$fluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl.

2. The compound according to claim 1, which is a compound of formula

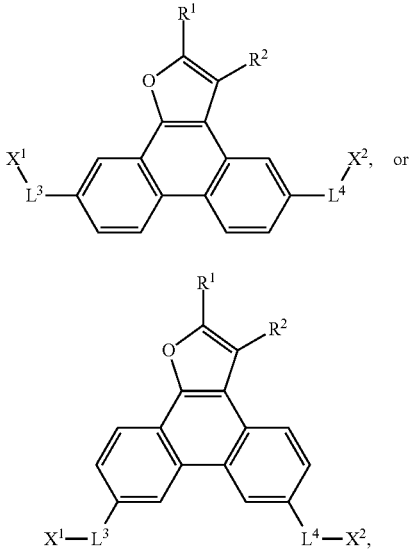

(Ia)

(Ib)

wherein $R^1$ and $R^2$ are a group of formula

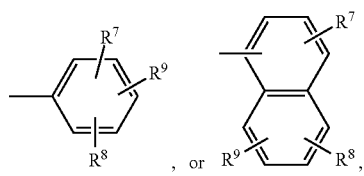

$R^7$, $R^8$ and $R^9$ are independently of each other H, $C_1$-$C_{18}$alkyl, $C_1$-$C_{18}$alkoxy, or $C_1$-$C_{18}$alkyl which is interrupted by O;

wherein -$L^3$-$X^1$ and -$L^4$-$X^2$ are independently of each other a group of formula -$NA^1A^{1'}$, or a group

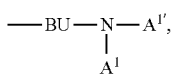

$A^1$ and $A^{1'}$ are independently of each other

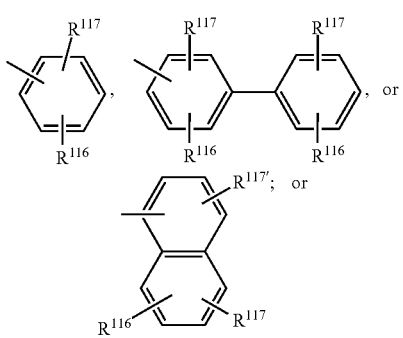

$A^1$ and $A^{1'}$ together with a nitrogen atom to which they are bonded form a heteroaromatic ring, or form a structure m' is 0, 1, or 2; m1 can be same or different at each occurrence and is 0, 1, 2, 3, or 4;

$R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{77}$, —C(=O)O$R^{78}$, or —C(=O)N$R^{75}R^{76}$, $R^{75}$, $R^{76}$ and $R^{78}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{77}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, BU is $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring selected from the group consisting of cyclohexyl and cyclopentyl, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(═O)—$R^{28}$, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —$SO_2$—, —O—, —$NR^{65}$—, —$SiR^{70}R^{71}$—, —$POR^{72}$—, —$CR^{63}$═$CR^{64}$—, or —C≡C—, and E is —$OR^{69}$, 13 $SR^{69}$, —$NR^{65}R^{66}$, —$COR^{68}$, —$COOR^{67}$, —$CONR^{65}R^{66}$, —CN, or halogen, G is E, or $C_1$-$C_{18}$alkyl, $R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl;

$R^{41}$ can be the same or different at each occurrence and is Cl, F, CN, $NR^{45}R^{45'}$, a $C_1$-$C_{25}$alkyl group, a $C_4$-$C_{18}$cycloalkyl group, a $C_1$-$C_{25}$alkoxy group, wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$;

$R^{45}$ and $R^{45'}$ are independently of each other a $C_1$-$C_{25}$alkyl group, a $C_4$-$C_{18}$cycloalkyl group, wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$;

-$L^3$-$X^1$ and -$L^4$-$X^2$ are independently of each other a group of formula

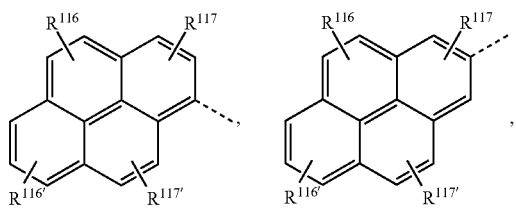

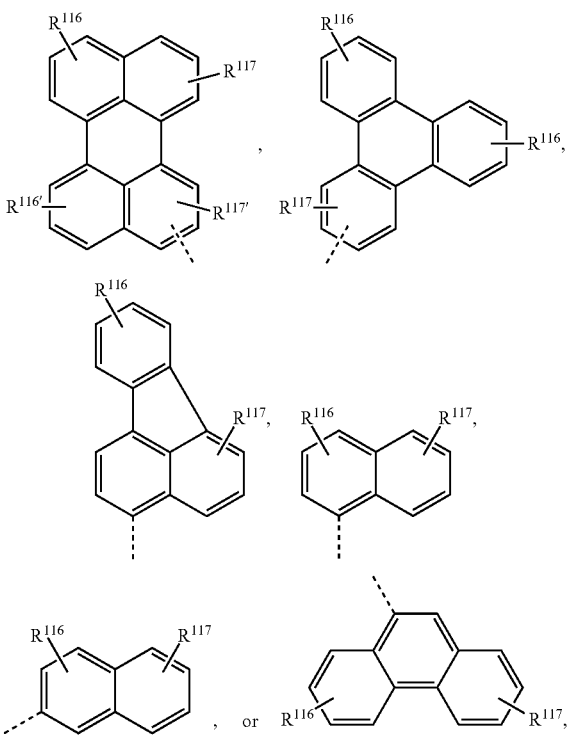

wherein $R^{116'}$ is same as $R^{116}$;

or

-$L^3$-$X^1$ and -$L^4$-$X^2$ are independently of each other a group of formula

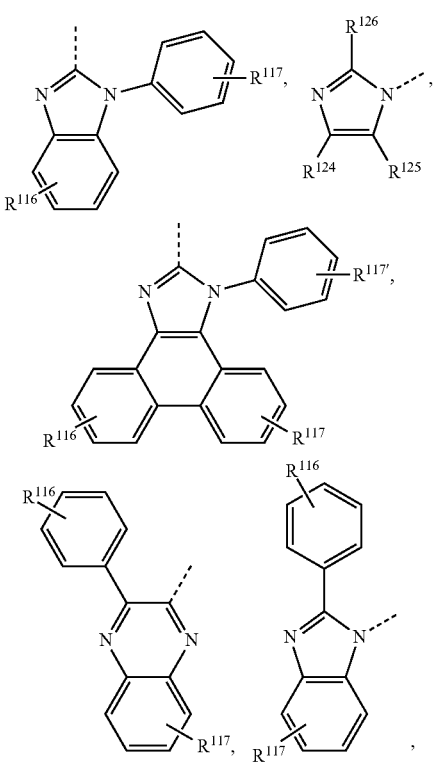

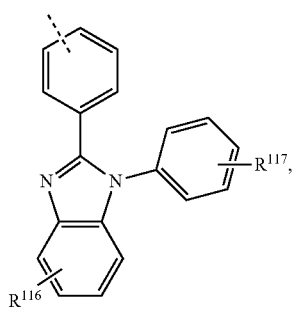

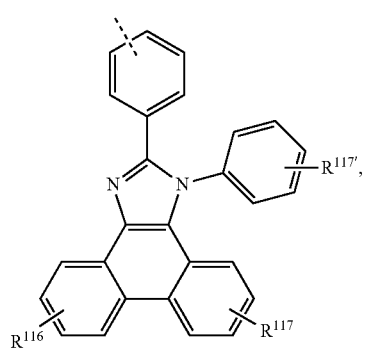

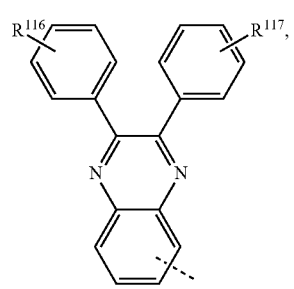

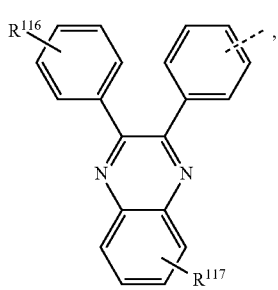

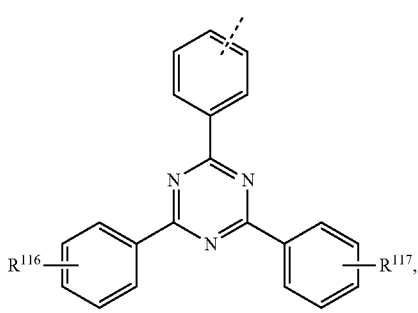

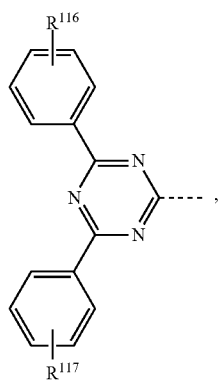

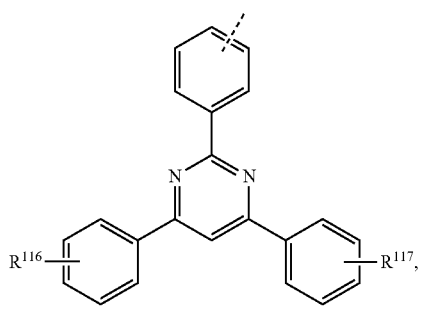

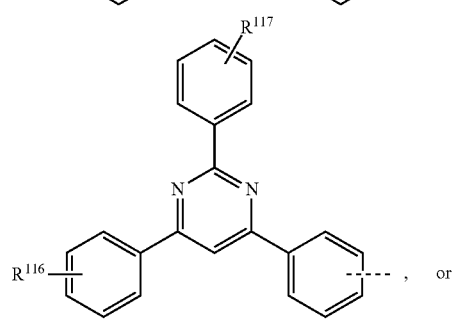

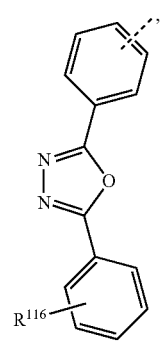

$R^{124}$, $R^{125}$ and $R^{126}$ are independently of each other H, $C_1$-$C_{18}$alkyl, $C_1$-$C_{18}$alkyl which is substituted by E and/or interrupted by D, $C_1$-$C_{18}$fluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl.

3. The compound according to claim 1, wherein -$L^3$-$X^1$ and -$L^4$-$X^2$ are independently of each other a group of formula -$NA^1A^{1'}$, or a group

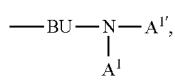

wherein

A¹ and A¹' are independently of each other

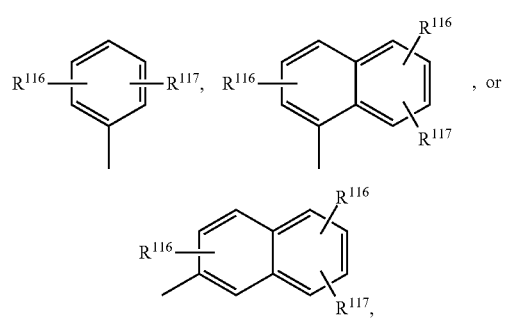

or A¹ and A¹' together with a nitrogen atom to which they are bonded form a group of formula

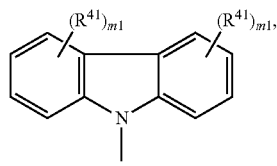

$R^{116}$ and $R^{117}$ are independently of each other $C_1$-$C_{18}$alkyl, which is optionally interrupted by —O—, or $C_1$-$C_{18}$alkoxy;

Bu is

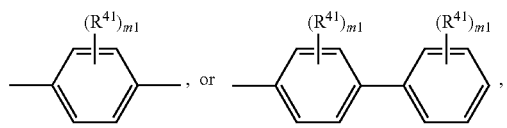

wherein $R^{41}$ can be same or different at each occurrence and is $C_1$-$C_{18}$alkyl, which is optionally interrupted by —O—, or $C_1$-$C_{18}$alkoxy; m1 is 0, 1, or 2.

4. The compound according to claim 1, wherein -$L^3$-$X^1$ and -$L^4$-$X^2$ are independently of each other a group of formula

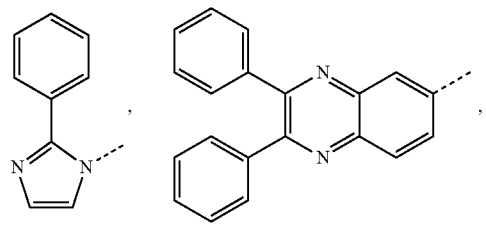

-continued

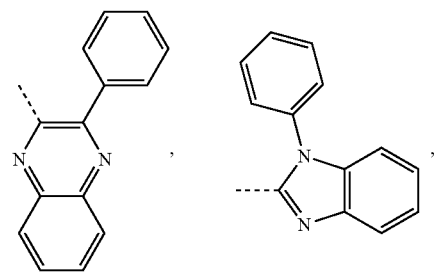

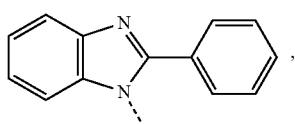

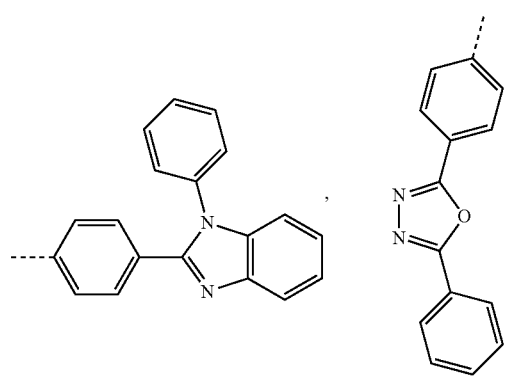

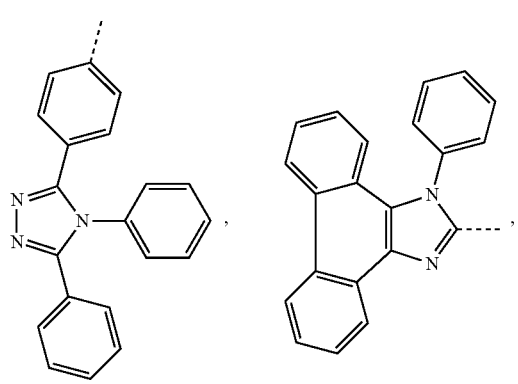

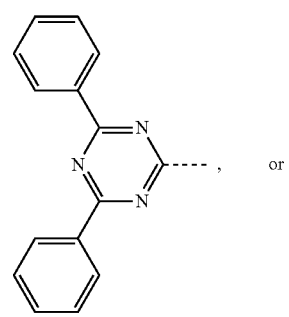

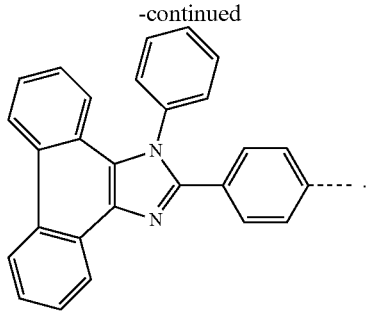

5. The compound according to claim 1,
wherein -L³-X¹ and -L⁴-X² are independently of each other a group of formula

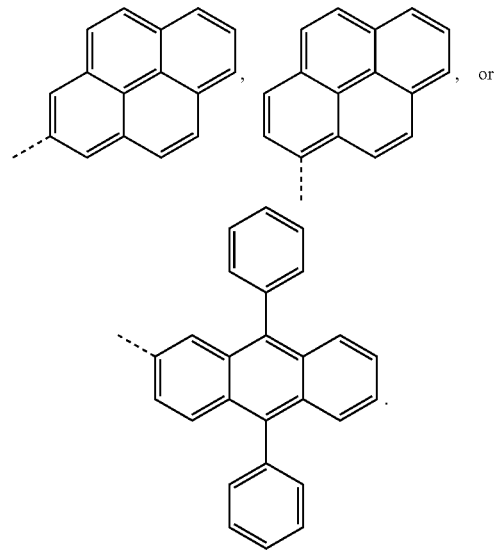

6. The compound according to claim 1, which is selected from the group consisting of

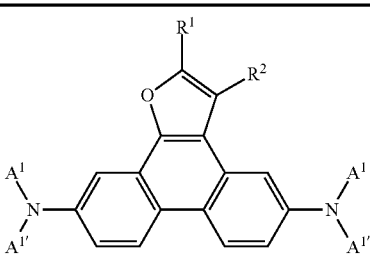

| Cpd. | R¹ = R² | A¹ | A¹' |
|---|---|---|---|
| A-1 | phenyl | phenyl | phenyl |
| A-2 | phenyl | phenyl | 1-naphthyl |

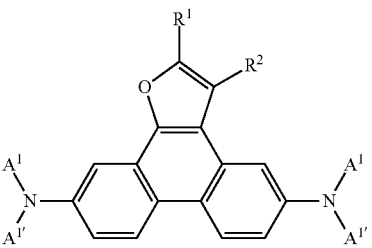

| Cpd. | R¹ = R² | A¹ | A¹' |
|---|---|---|---|
| A-3 | 1-naphthyl | phenyl | 1-naphthyl |
| A-4 | 1-naphthyl | phenyl | phenyl |
| A-5 | phenyl | 3-tolyl | 3-tolyl |
| A-8 | phenyl | 2) | 2) |

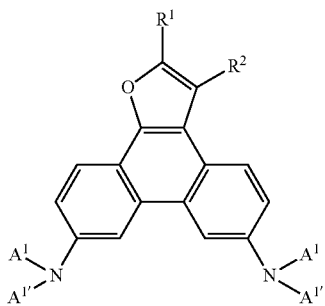

| Cpd. | R¹ = R² | A¹ | A¹' |
|---|---|---|---|
| B-1 | phenyl | phenyl | phenyl |
| B-2 | phenyl | phenyl | 1-naphthyl |

-continued

| Cpd. | R¹ = R² | A¹ | A¹' |
|---|---|---|---|
| B-3 | naphthyl | phenyl | naphthyl |
| B-4 | naphthyl | phenyl | phenyl |
| B-5 | phenyl | tolyl | tolyl |
| B-8 | phenyl | 2) | 2) |

| Cpd. | R¹ = R² | X¹ | X² |
|---|---|---|---|
| C-1 | phenyl | AR-1 | AR-1 |
| C-2 | phenyl | AR-2 | AR-2 |
| C-3 | phenyl | AR-3 | AR-3 |

| Cpd. | R¹ = R² | X¹ | X² |
|---|---|---|---|
| D-1 | phenyl | AR-1 | AR-1 |
| D-2 | phenyl | AR-2 | AR-2 |
| D-3 | phenyl | AR-3 | AR-3 |

| Cpd. | R¹ = R² | X¹ | X² |
|---|---|---|---|
| E-1 | phenyl | HE-1 | HE-1 |
| E-2 | phenyl | HE-2 | HE-2 |
| E-3 | phenyl | HE-3 | HE-3 |
| E-4 | phenyl | HE-4 | HE-4 |
| E-5 | phenyl | HE-5 | HE-5 |
| E-6 | phenyl | HE-6 | HE-6 |

-continued

| Cpd. | R¹ = R² | X¹ | X² |
|---|---|---|---|
| E-8 | phenyl | HE-8 | HE-8 |
| E-9 | phenyl | HE-9 | HE-9 |
| E-19 | phenyl | HE-10 | HE-10 |

| Cpd. | R¹ = R² | X¹ | X² |
|---|---|---|---|
| F-1 | phenyl | HE-1 | HE-1 |
| F-2 | phenyl | HE-2 | HE-2 |
| F-3 | phenyl | HE-3 | HE-3 |
| F-4 | phenyl | HE-4 | HE-4 |
| F-5 | phenyl | HE-5 | HE-5 |
| F-6 | phenyl | HE-6 | HE-6 |

-continued

| Cpd. | R¹ = R² | X¹ | X² |
|---|---|---|---|
| F-8 | phenyl | HE-8 | HE-8 |
| F-9 | phenyl | HE-9 | HE-9 |
| F-19 | phenyl | HE-10 | HE-10 |

2) A¹ and A¹' together form a group (N-methylcarbazole),

AR-1 is (pyrene),

AR-2 is (pyrene),

AR-3 is (9,10-diphenylanthracene),

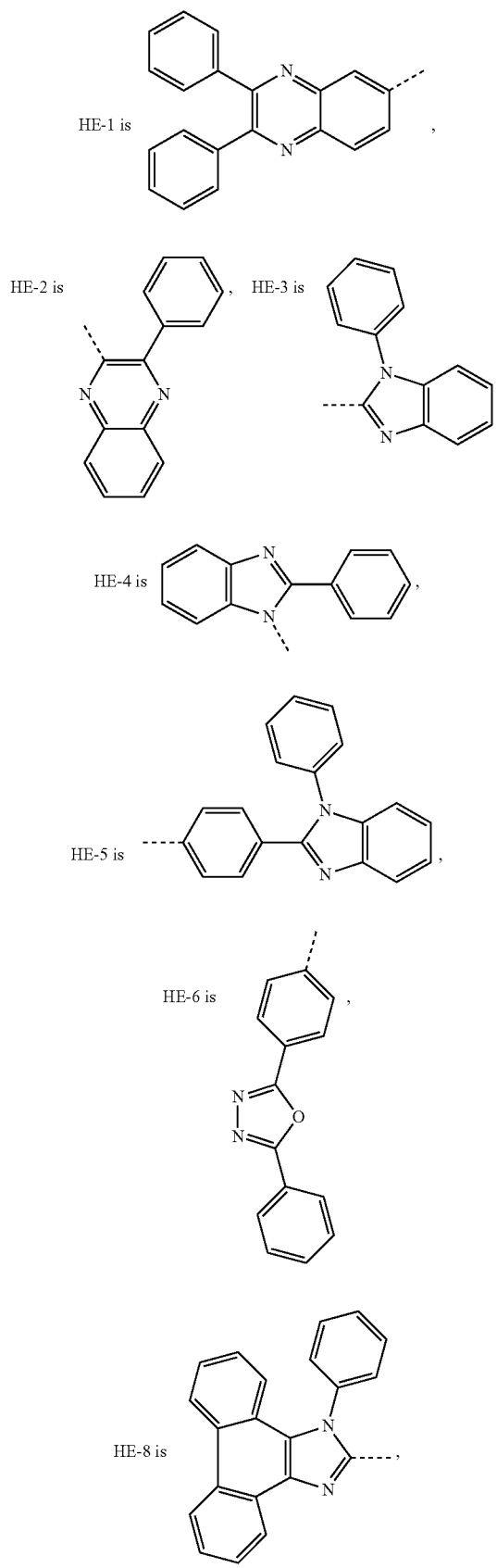
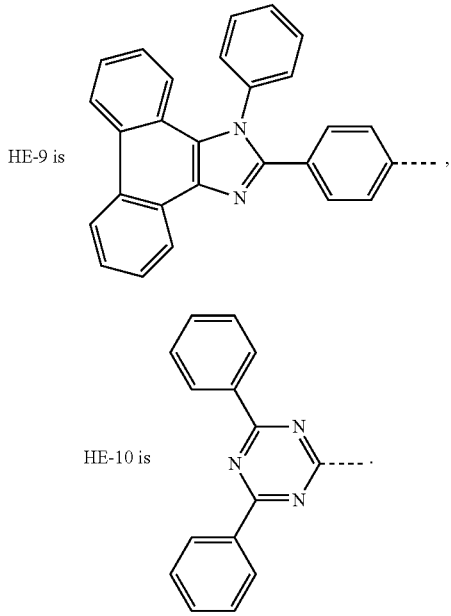
7. A process for preparing the compound according to claim 1, comprising:
reacting a compound of formula
$$\text{(II)}$$
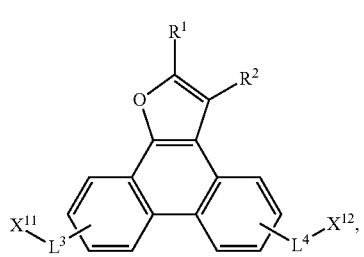
with a compound of formula $HNA^1A^{1'}$,
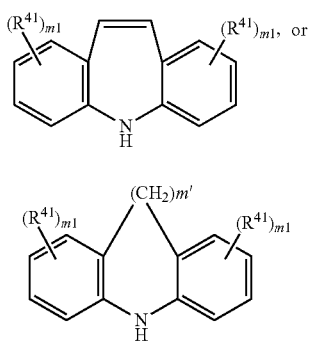
in the a presence of a base and a catalyst in a solvent,
wherein $X^1$ and $X^2$ are independently of each other $-NA^1A^{1'}$,

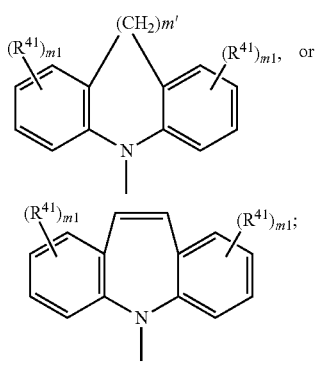

m' is 0, 1, or 2;
wherein $X^{11}$ and $X^{12}$ stand for halogen,
wherein
$A^1$ and $A^{1'}$ are independently of each other

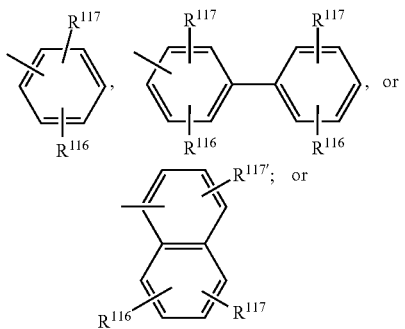

$A^1$ and $A^{1'}$ together with the nitrogen atom to which they are bonded form a heteroaromatic ring, or form a structure

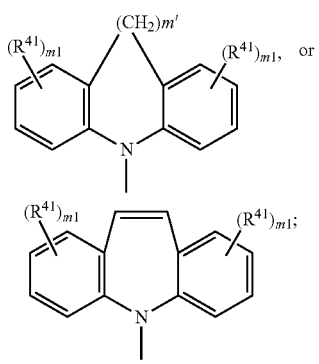

m1 can be same or different at each occurrence and is 0, 1, 2, 3, or 4;
$R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{77}$, —C(=O)O$R^{78}$, or —C(=O)N$R^{75}R^{76}$, $R^{75}$, $R^{76}$ and $R^{78}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
$R^{77}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
wherein $L^3$ and $L^4$ are independently of each other a single bond, or a bridging unit BU,
BU is

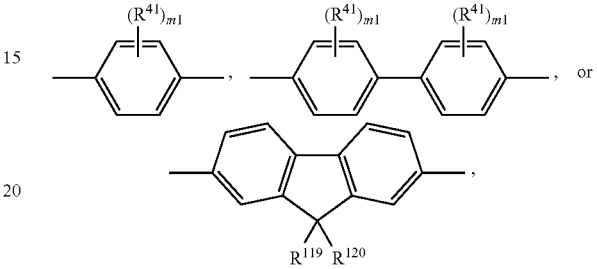

$R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or
$R^{119}$ and $R^{120}$ together form a group of formula =$CR^{121}R^{122}$, wherein
$R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or
$R^{119}$ and $R^{120}$ together form a five or six membered ring selected from the group consisting of cyclohexyl and cyclopentyl, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{28}$,
$R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
D is —CO—, —COO—, —S—, —SO—, —SO$_2$—, —O—, —N$R^{65}$—, —Si$R^{70}R^{71}$—, —PO$R^{72}$—, —C$R^{63}$=C$R^{64}$—, or —C≡C—, and
E is —O$R^{69}$, —S$R^{69}$, —N$R^{65}R^{66}$, —CO$R^{68}$, —COO$R^{67}$, —CON$R^{65}R^{66}$, —CN, or halogen,
G is E, or $C_1$-$C_{18}$alkyl,
$R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl;

wherein $R^1$ and $R^2$ are a group of formula

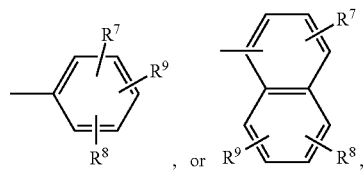

$R^7$, $R^8$ and $R^9$ are independently of each other H, $C_1$-$C_{18}$alkyl, $C_1$-$C_{18}$alkoxy, or $C_1$-$C_{18}$alkyl which is interrupted by O;

$R^{205}$, $R^{206}$, $R^{207}$, and $R^{208}$ are independently of each other H, $C_1$-$C_{18}$alkyl, $C_1$-$C_{18}$alkyl which is interrupted by O, $C_1$-$C_{18}$alkoxy, or $C_1$-$C_{18}$alkoxy which is interrupted by O, or $C_1$-$C_{18}$fluoroalkyl;

wherein $R^{41}$ can be the same or different at each occurrence and is Cl, F, CN, $NR^{45}R^{45'}$, a $C_1$-$C_{25}$alkyl group, a $C_4$-$C_{18}$cycloalkyl group, a $C_1$-$C_{25}$alkoxy group, wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$;

$R^{45}$ and $R^{45'}$ are independently of each other a $C_1$-$C_{25}$alkyl group, a $C_4$-$C_{18}$cycloalkyl group, wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$.

* * * * *